US010343161B2

(12) United States Patent
Delamarche et al.

(10) Patent No.: US 10,343,161 B2
(45) Date of Patent: *Jul. 9, 2019

(54) CUSTOMIZABLE MICROFLUIDIC DEVICE WITH PROGRAMMABLE MICROFLUIDIC NODES

(71) Applicant: INTERNATIONAL BUSINESS MACHINES CORPORATION, Armonk, NY (US)

(72) Inventors: Emmanuel Delamarche, Thalwil (CH); Onur Gökçe, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 4 days.

This patent is subject to a terminal disclaimer.

(21) Appl. No.: 15/630,980

(22) Filed: Jun. 23, 2017

(65) Prior Publication Data

US 2018/0369813 A1    Dec. 27, 2018

(51) Int. Cl.
*B01L 3/00*       (2006.01)
*F16K 99/00*    (2006.01)
*G01N 21/01*   (2006.01)

(52) U.S. Cl.
CPC .... *B01L 3/502738* (2013.01); *F16K 99/0003* (2013.01); *F16K 99/0034* (2013.01);
(Continued)

(58) Field of Classification Search
CPC ...... G06F 2271/02; G06F 9/06; B01L 3/5027; B01L 2208/027; B91C 1/0019;
(Continued)

(56) References Cited

U.S. PATENT DOCUMENTS 9,409,173 B2      8/2016   Estes et al.
2005/0249641 A1*  11/2005  Blankenstein .... B01L 3/502738
                                                                          422/400
(Continued)

FOREIGN PATENT DOCUMENTS

WO    2016122552 A1   8/2016
WO    2018235013 A1   12/2018
WO    2018235014 A1   12/2018

OTHER PUBLICATIONS

Kang et al., "Buckling delamination induced microchannel: Flow regulation in microfluidic devices," Article in Applied Physics Letters, Sep. 2016, Published by AIP Publishing, Appl. Phys. Lett. 102, 031902 (2013); 10.1063/1.4788734, pp. 1-6.
(Continued)

*Primary Examiner* — Phallaka Kik
(74) *Attorney, Agent, or Firm* — Jordan T. Schiller

(57) ABSTRACT

The invention is directed to a microfluidic device. The device includes an input microchannel, a set of m distribution microchannels, a set of m microfluidic modules and a set of m nodes. The m microfluidic modules (m≥2) are in fluidic communication with the m distribution microchannels, respectively. The one or more nodes of the set of m nodes branch from the input microchannel, and further branch to a respective one of the set of m distribution microchannels. In addition, a subset, but not all, of the nodes are altered. The nodes of the set of m nodes have different liquid pinning strengths. As a result, the extent in which a liquid passes through one or more of the m microfluidic modules varies based on the different liquid pinning strengths, in operation. Additional sets of nodes may be provided to allow liquid to pass through ordered pairs of modules.

25 Claims, 12 Drawing Sheets

(52) U.S. Cl.
CPC ............... *G01N 21/01* (2013.01); *B01L 3/50* (2013.01); *B01L 2300/123* (2013.01); *B01L 2400/06* (2013.01); *F16K 99/0001* (2013.01); *G06F 2217/02* (2013.01); *G06F 2217/06* (2013.01)

(58) Field of Classification Search
CPC ............... F16K 99/003; F16K 99/0034; F16K 99/0001; G01N 3/50
USPC ....... 716/30; 435/5, 29, 31, 387.11, 387, 11; 436/71, 86, 94; 422/502, 552
See application file for complete search history.

(56) References Cited

U.S. PATENT DOCUMENTS

| | | |
|---|---|---|
| 2011/0098597 A1 | 4/2011 | Wu |
| 2012/0241013 A1 | 9/2012 | Linder et al. |
| 2013/0043170 A1 | 2/2013 | Rose |
| 2014/0099722 A1 | 4/2014 | Boudot et al. |
| 2014/0230909 A1 | 8/2014 | Di Carlo et al. |
| 2015/0132742 A1 | 5/2015 | Thuo et al. |
| 2016/0101419 A1 | 4/2016 | Li |
| 2016/0279632 A1 | 9/2016 | Delamarche et al. |
| 2017/0029871 A1 | 2/2017 | Ying |
| 2017/0120240 A1 | 5/2017 | Delamarche |
| 2017/0350821 A1 | 12/2017 | Delamarche |
| 2018/0369809 A1 | 12/2018 | Delamarche |
| 2018/0372765 A1 | 12/2018 | Delamarche |

OTHER PUBLICATIONS

Ahn et al., "Disposable Smart Lab on a Chip for Point-of-Care Clinical Diagnostics," Proceedings of the IEEE, vol. 92, No. 1, Jan. 2004, Copyright 2004 IEEE, pp. 154-173.

Liu et al., "Self-Contained, Fully Integrated Biochip for Sample Preparation, Polymerase Chain Reaction Amplification, and DNA Mircoarray Detection," Anal. Chem. 2004, 76, pp. 1824-1831, © 2004 American Chemical Society Published on Web Feb. 25, 2004.

Satoh et al., "Electrowetting-based valve for the control of the capillary flow," Journal of Applied Physics 103, 034903, 2008 (Best Date Available), © 2008 American Institute of Physics. fDOI: 10.1063/1.2832629g, pp. 034903-1-034903-9.

Zoval et al., "Centrifuge-Based Fluidic Platforms," Roceedings of the IEEE, vol. 92, No. 1, Jan. 2004, © 2004 IEEE, pp. 140-153.

IBM: List of IBM Patents or Patent Applications Treated as Related (Appendix P), Jun. 23, 2017, pp. 1-2.

Pending U.S. Appl. No. 15/630,982, filed Jun. 23, 2017, titled "Microfluidic Device With Multi-Level, Programmable Microfluidic Node,", pp. 1-43.

Pending U.S. Appl. No. 15/630,991, filed Jun. 23, 2017, titled "Microfluidic Device With Programmable Verification Features,", pp. 1-81.

Carrilho et al., "Understanding Wax Printing: A Simple Micropatterning Process for Paper-Based Microfluidics," Analytical Chemistry, Aug. 15, 2009, p. 7091-7095, vol. 81, No. 16, American Chemical Society.

* cited by examiner

CUSTOMIZABLE MICROFLUIDIC DEVICE WITH PROGRAMMABLE MICROFLUIDIC NODES

BACKGROUND

The invention relates in general to the field of microfluidic devices and methods of functionalization and configuration of such devices.

Microfluidics deals with the precise control and manipulation of small volumes of fluids that are typically constrained to micro scale channels and to volumes typically in the millimeter range. Prominent features of microfluidics originate from the peculiar behavior that liquids exhibit at the micro scale. Flow of liquids in microfluidics is typically laminar. Volumes well below one nanoliter can be reached by fabricating structures with lateral dimensions in the micrometer range. Microfluidic devices generally refer to microfabricated devices, which are used for pumping, sampling, mixing, analyzing and dosing liquids.

Many microfluidic devices have user chip interfaces and closed flow paths. Closed flow paths facilitate the integration of functional elements (e.g., heaters, mixers, pumps, UV detector, valves, etc.) into one device while minimizing problems related to leaks and evaporation. The analysis of liquid samples often requires a series of steps (e.g., filtration, dissolution of reagents, heating, washing, reading of signal, etc.).

In general, microfluidic devices are designed in view of a restricted set of applications, typically one application only. Thus, new designs of microfluidic devices are typically needed for each new application, which impacts the costs of the devices.

SUMMARY

According to a first aspect, the present invention is embodied as a microfluidic device. The device comprises an input microchannel, a set of m distribution microchannels, a set of m microfluidic modules and a set of m nodes. The set of m microfluidic modules (m≥2) are in fluidic communication with the set of m distribution microchannels, respectively. One or more node of the set of m nodes branches from the input microchannel and further branches to a respective one of the set of m distribution microchannels, so as to potentially ensure fluidic communication from the input microchannel to the respective one of the set of m distribution microchannels it branches to. In addition, a subset, but not all, of the nodes of the set of m nodes are altered, compared with remaining nodes of the set of m nodes. Due to this alteration, the nodes in the set of m nodes have different liquid pinning strengths. As a result, the extent in which a liquid introduced in the input microchannel passes through one or more of the set of m microfluidic modules varies based on the different liquid pinning strengths of the nodes (which depend on the alteration states of the nodes), in operation.

In other words, the microfluidic circuit can be configured based on the alteration states of the nodes. As a result, downstream microfluidic modules may be reached by liquid introduced in the input microchannel (e.g., after a certain period), or not, depending on the configuration of the nodes. This, as one understands, allows a microfluidic device to be "programmed" by altering some of the nodes.

In simplest embodiments, the nodes are altered to act in a binary fashion. For example, some of the nodes of the set of m nodes are altered, compared with remaining nodes of that set, so as for one or more of the set of m nodes to either pin a liquid thereat or let a liquid pass there-through.

In preferred embodiments, the microfluidic device is designed so as to allow liquid to pass through ordered pairs of modules. To that aim, the device includes m additional sets of nodes, in addition to the first set of m nodes. The m additional sets of nodes include m nodes each, such that the microfluidic device includes m+1 sets of m nodes. The device further includes a set of m output microchannels, wherein one or more of the set of m output microchannels connects to an output of a respective one or more of the set of m microfluidic modules. The set of m output microchannels are associated with the m additional sets of nodes. That is, one or more of the set of m output microchannels branches into one or more of the set of m nodes of a respective one of the m additional sets of m nodes. Furthermore, one or more node of the respective one of the m additional sets of m nodes branches to a respective one of the distribution microchannels. In other words, one or more node of the respective one of the m additional sets of m nodes connects an output channel to a distribution channel. In addition, some of the m nodes of at least one of the m additional sets are altered. That is, for at least a given one of the m additional sets of nodes: a subset, but not all, of the m nodes are altered, compared with remaining nodes of this set of m nodes. Thus, the m nodes of this set exhibit different liquid pinning strengths. As a result, the extent in which a liquid introduced in the input microchannel passes through one or more ordered pairs of two, or set, of the m microfluidic modules varies according to the different liquid pinning strengths of the nodes of the first set of m nodes and said given one or more of the m additional sets, in operation. That is, liquid introduced in the input microchannel passes through at least one ordered pair, or set, of the m microfluidic modules. In other words, liquid passes through two or more of the modules, in an order determined by the different liquid pinning strengths of the nodes. Yet, the extent in which ordered pairs of modules are effectively fluidly connected (for liquid to pass from one module to the other) is determined by the different liquid pinning strengths of the nodes of the first set and said given one of the m additional sets, in operation.

Accordingly, even though any ordered pair of modules are potentially connected via interconnecting nodes, the actual alteration states of the interconnecting nodes give rise to different pinning strengths, which, in turn, determine the extent in which liquid introduced in the input channel will effectively pass through ordered pairs, or set, of modules. The actual number of ordered pairs effectively enabled and the extent in which such pairs are enabled depend on the alteration states of all of the nodes.

Now, it may not be necessary to connect all potential pairs of modules in practice. That is, each additional set of nodes may comprise less than m nodes each. For example, assuming that nodes connecting each module to itself can be removed, the m additional sets may only include m−1 nodes each. More generally, each of the m additional sets of nodes may in fact restrict to a few nodes only, or even to a single node. Generalizing this principle, the present microfluidic devices may, in embodiments, include at least two microfluidic modules, a first set of at least two nodes (each connecting the input microchannel to a respective one of the modules, e.g., thanks to distribution channels, as in previous embodiments) and a second set of at least two nodes (each connecting a pair of distinct ones of the microfluidic modules). For example, the second set of nodes here corresponds to a superset formed by m additional sets of nodes that include, each, at least one node. Consistently with the above principles, a subset, but not all, of the nodes of each of the first set and the second set may be altered, compared with remaining nodes of said sets, so as to have different liquid pinning strengths. As a result, the extent in which a liquid introduced in the input microchannel passes through one or more ordered pairs of modules varies according to the different liquid pinning strengths of the nodes, in operation. That is, liquid introduced in the input microchannel passes through at least one ordered pair of the microfluidic modules but the extent in which ordered pairs of modules are effectively fluidly connected depends on the alteration state of the nodes, as in the previous case.

In preferred embodiments, each node of either set may be configured so as to either pin a liquid thereat or let a liquid pass there-through, as noted above. In more sophisticated variants, the nodes of the first set may allow a liquid (as initially introduced in the input channel) to reach distinct modules at distinct times, owing to their different pinning strengths. Moreover, additional nodes may be configured so as to allow liquid exhausted from said distinct modules to subsequently reach other modules.

Although the additional set of nodes may comprise a reduced number of nodes (i.e., at least one node and at most m nodes each), it may, however, be simpler to design microfluidic devices that comprise m+1 sets of m nodes each, especially when willing to achieve a multi-purpose device. Having m additional sets of m nodes each means that each module may potentially be connected to itself, via "diagonal" nodes. However, such nodes may typically not be configured so as to effectively allow liquid exhausted by a given module to later re-enter that same module. Moreover, even if such diagonal nodes are altered so as to allow, in principle, liquid to pass there-through, the presence of liquid in the respective one of the set of m distribution microchannels may simply prevent liquid exhausted by a given module to re-enter that same module. More generally, one understands that the respective one or more node of the m additional sets of m nodes and the respective one of the set of m distribution microchannels may be configured so as to effectively prevent liquid exhausted by a given one or more of the set of m microfluidic modules to later re-enter the same one or more of the set of m microfluidic modules.

In embodiments, the microfluidic device includes m+1 sets of m nodes, which are arranged as an array of m×(m+1) nodes, in a crossbar switch configuration, which makes it easier to design and program the device.

Preferably, the present microfluidic devices include distinct, parallel levels (including a first level and a second level). Both the input microchannel and the set of m output microchannels are defined on the first level, whereas the set of m distribution microchannels are defined on the second level. This allows non-parallel, 3D channel configurations, where, e.g., both the input channel and the output channels are arranged parallel to a first direction, on a first level, whereas the distribution channels are arranged parallel to a second direction (transverse to the first direction), on a second level. Such transverse configurations allow more compacts arrangements of the channels to be designed and, in turn, devices of reduced footprints to be achieved.

In preferred embodiments, 3D nodes are relied upon, which may advantageously be used to enable transverse, 3D channel configurations as described above. For example, at least a subset of the nodes may include, each: a cavity; an inlet port; an outlet port; and a via. The cavity is formed on the first level and is open on top. The inlet port too is formed on the first level; it branches from the input microchannel or one of the set of m output microchannels, consistently with arrangements as discussed above. The inlet port further communicates with the cavity through an ingress thereof. Meanwhile, the outlet port branches to one of the set of m distribution microchannels on the second level. The via extends from the cavity (e.g., from a bottom side thereof) to the outlet port, so as for the cavity to communicate with the outlet port. In addition, the cavity comprises (e.g., includes or is closed off by) a liquid blocking element, which is configured to prevent an aqueous liquid filling the inlet port to reach the outlet port of the node.

That the cavity be open on top makes it easy to fabricate and, all the more, this makes the cavity easily accessible from the top, in order to alter the pinning strength of the liquid blocking element. This way, a multi-level node is achieved, which allows a multi-level microfluidic circuit as described above to be configured (and possibly re-configured) based on the alteration state of the blocking element of the cavity.

Preferably, the via extends on an intermediate level, or a third level, of the device, between the first level and the second level. More preferably, the via extends from a bottom side of the cavity (opposite to the top side) down to the outlet port. Having vias extending from the bottom side of the cavity eases the fabrication of the nodes, as vias may be open in the cavity, from the top. Meanwhile, imposing an intermediate level (in which vias are formed) between outer levels (in which channels are formed) eases the design of devices with transverse channel configurations. For example, the intermediate level prevents short-circuits between transverse channels.

In embodiments, the liquid blocking element is a liquid pinning structure formed at the ingress of the cavity. The pinning structure is configured to stop, or prevent, a liquid filling front of an aqueous liquid at the ingress of the cavity. Such a design makes it particularly simple to activate the cavity. Indeed, as the pinning structure is arranged at the ingress of the cavity, room left vacant in the cavity can conveniently be exploited to spot a wetting material or otherwise alter the pinning structure, in order to alter the pinning strength of the node. Still, the device may be sealed, at a later stage, e.g., by covering all open structures on top with a lid (e.g., by laminating a polymeric film), as usual in the art.

Preferably, the liquid pinning structure is formed by an opening angle $\theta_1$ of the cavity, wherein the opening angle is between 90° and 160°. For example, this angle may simply be of 90°, i.e., formed by a straight wall (extending perpendicularly to the liquid inlet direction), to which the inlet port leads. In more sophisticated embodiments, this angle is strictly larger than 90°, it may for example be of 135°. In all cases, considering a situation where liquid fills the inlet port with an advancing contact angle, the enlargement, i.e., the widening at the entrance in the cavity adds an angle component that challenges the propagation of the meniscus into the cavity. In variants, the opening angle may be less than 90°, e.g., between 60° and 90°, provided that lateral walls of the cavity supporting this angle are hydrophobic.

In preferred embodiments, the ingress of the cavity has a width that is smaller than the depth. Walls of the cavity, on each side of the ingress, are separated by a gap corresponding to the width of the ingress. Said walls, accordingly, form two opposite opening angles $\theta_1$ in the cavity, wherein the opening angles, respectively, are between 60° and 160°, as explained above. The inlet port may for instance extend along a main axis of the cavity, so as for the ingress to be centered in the cavity. This way, two lateral edges are formed at the ingress, which form the two opening angles and challenge the propagation of a meniscus into the cavity. Since, in addition, the depth of the ingress is larger than the width, liquid that gets laterally pinned at the ingress of the cavity cannot overcome the pinning barrier by wetting both a bottom of the inlet port and cavity and an opposite lid, in operation. Thus, the cavity is disabled by default (i.e., normally OFF) in that case, meaning that only those nodes that need be activated (for programming purposes) will be altered, which is simply achieved thanks to the open cavity. Most simple is to have the ingress centered at the entrance of the cavity, to maximize the pinning strength of the lateral edges.

In variants, the ingress may be more or less off-centered, laterally. If the ingress is completely off-centered, then liquid "sees" only one edge at the entrance of the cavity, which may to partial liquid pinning only.

A node as defined above (i.e., with a liquid pinning structure forming one or two opening angles) may for instance be altered thanks to a wetting material arranged at the liquid pinning structure, so as to allow an aqueous liquid filling the inlet port to reach the outlet port, notwithstanding the liquid pinning structure.

In variants to such liquid pinning structures, the blocking element may be formed by an alterable element, such as a hydrophobic barrier, placed in the cavity or sealing the cavity on the bottom side, opposite the top side. For example, a hydrophobic barrier may be used, which is a removable substance (e.g., wax), inserted in the cavity. The alterable element may else be a thin-film sealing the cavity from below. Such designs were found to be particularly convenient when using wicking media (like fibrous/porous media such as paper or nitro-cellulosic materials) as a basis to form the various flow paths.

In embodiments, the inlet ports of two nodes of a same set of nodes (i.e., nodes that branch from a same channel) have different hydraulic resistances, e.g., to compensate for the differences in flow rates of liquid reaching those inlet ports.

In preferred embodiments, the outlet port of a node comprises a fluid flow constriction valve, so as to prevent an aqueous liquid in the set of m distribution microchannels, branched by the outlet port, to enter the node and reach the via. This way, fully unidirectional nodes are achieved, which allow ordered pairs of modules to be fluidly connected, in one direction only.

Preferably, the output port branches, at a level of a junction, to a respective one of the set of m distribution microchannels that comprises a fluid flow constriction valve on one side at the level of the junction, so as to force an aqueous liquid exhausted through the outlet port toward a direction that extends from the one side at the level of the junction to an opposite side at the level of the junction. Thus, the outlet port and the valve of the distribution microchannel work as a diode, which makes it possible for a column of unidirectional nodes to branch to a same distribution microchannel.

The fluid flow constriction valve on one side at the level of the junction may for example be formed by a first section and a second section of the respective one of the set of m distribution microchannels branched by the outlet port. The first section is tapered and leads to the second section, which has a larger average diameter than the first section, so as to provide an opening angle $\theta_2$ in the second section, which is between 90° and 160°.

The present devices are preferably dimensioned as follows. Each of the input microchannel, the one or more of the set of m distribution microchannels and the one or more of the set of m output microchannels have a depth that is between 10 and 100 µm. Meanwhile, each of the input microchannel, the one or more of the set of m distribution microchannels and the inlet port have a same depth and the inlet port has a width that is between 5 and 50 µm. On the other hand, the via has an average diameter that is between 25 and 200 µm, as measured parallel to a mid-plane of the first level from the second level.

In preferred embodiments, the present devices are fabricated as multi-layered devices. Each layer may for instance house one or more levels of the devices, as discussed earlier. In variants, each level may require one or more material layers, depending on the fabrication technique chosen, as discussed in detail in the next section. For example, the present microfluidic devices may comprise at least two layers, wherein the input microchannel and the one or more of the set of m output microchannels, the cavity and the inlet port are all formed in a first layer of the at least two layers, whereas the one or more of the set of m distribution microchannels are formed in a second layer of the at least two layers. In variants, the devices may be obtained in a single injection molding step.

In embodiments, the present devices comprise at least three layers. The via of the cavity may for example be formed in an intermediate layer, between a first layer and a second layer of the device.

The microfluidic modules typically have different functions. The set of m microfluidic modules may notably comprise two or more of: an optical detection chamber (configured in the device so as to enable optical detection); a fluid mixing chamber; and a reaction chamber. Embodiments are described in the next section, which notably involve a set of m=2, 3, 4, 8 or 36 distinct modules, which allows various microfluidic applications.

According to another aspect, the invention can be embodied as a method of programming a microfluidic device such as described above, which revolves around altering a subset of the nodes of the device, so as to confer different liquid pinning strengths to the nodes, consistently with principles discussed above. Aspects of such methods are evoked in the detailed description of the present devices, in the next section.

Microfluidic devices and methods embodying the present invention will now be described, by way of non-limiting examples, and in reference to the accompanying drawings.

Figure 1:
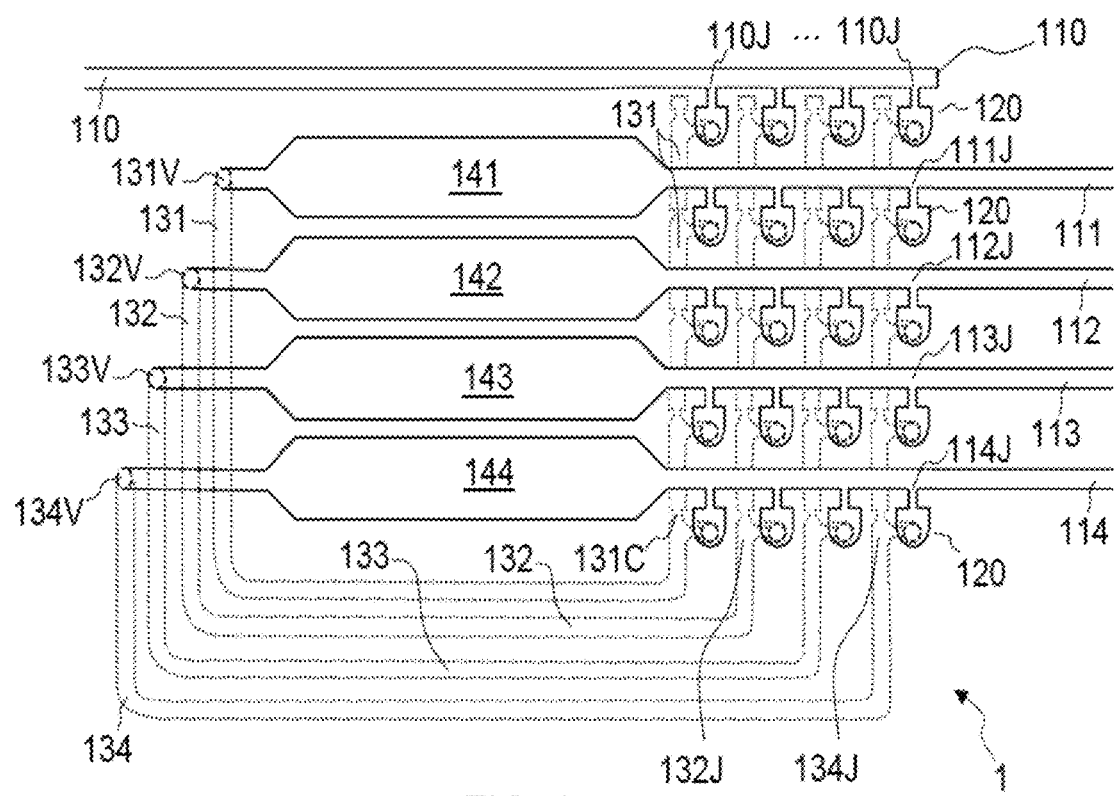
FIG. 1 is a top view of a microfluidic device with a transverse channel configuration and a programmable array of nodes in a crossbar switch configuration, the device 3D fabricated in silicon, according to a first class of embodiments.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

In the following, a shorthand notation is used, on occasion, for numeral references. For example, the notation "k20", where k=1, . . . , 6, may be used in place of numeral references 120, . . . , 620. Thus, the notation "k20" encompasses numeral references 120, 420, and 620, which pertain to microfluidic nodes of different microfluidic devices 1, 4 and 6, respectively depicted in FIGS. 1, 7 and 10.

In the following, a shorthand notation is used, on occasion, for numeral references. For example, the notation "k1*l*", where k=1, . . . , 6, and where l=1, . . . , 8 may be used in place of numeral references. Also for example, the notation "k1*l*" may encompass numeral references such as 111-114, 411-414, and 511-518, which pertain to output channels, respectively depicted in FIGS. 1, 4, 7A-7B and 10, respectively. Also for example, the notation "k3*l*" may encompass numeral references such as 131-134 and 431-434, which pertain to distribution channels, as depicted in FIGS. 1, 7A-7B, and 8, respectively. Also for example, the notation "k4*l*" may encompass numeral references such as 141-144 and 441-444, which pertain to microfluidic modules, as depicted in FIGS. 1, 4, 7A-7B, and 8, respectively.

In describing various embodiments of the invention, reference may be made to "each" element in a set (e.g., "Each additional set of m nodes branches from a given one of the output microchannels . . . "); it should be noted that use of the word "each" is for illustrative purposes only, and that embodiments of the invention may be practiced using fewer than each element discussed, as recited in the claims.

In reference to FIGS. 1, 4-9, an aspect of the invention is first described, which concerns microfluidic devices k (with k=1, . . . , 6). Such microfluidic devices comprise microchannels and other microfluidic features, a characteristic dimension of which (e.g., width or depth) is in the micrometer-length range, i.e., typically between 1 μm and 100 μm. Yet, some particular structures of such devices may be in the nanoscale range or in the millimeter range, the devices as a whole typically being in the centimeter range.

Such devices k typically have the following, minimal configuration: they include an input microchannel k10, a set of m distribution microchannels k3*l*, a set of m microfluidic modules k4*l* and a set of m nodes k20, where m≥2.

The m microfluidic modules k4*l* are in fluidic communication with the m distribution microchannels k3*l*, respectively. In this description, terminologies such as "fluidic communication", "in fluid communication with" or "fluidically connected to" refer to one and a same concept, whereby a liquid is allowed to pass from one of the part to the other, through a passage, a channel, a via or any other suitably designed connection. Now, if a microfluidic node is intercalated on the fluidic path, then one potentially has a "fluidic communication" (or "fluidic connection"). However, the extent in which fluidic communication is enabled depends on the alteration state of the node, as explained below.

The m nodes k20 branch, each, from the input microchannel k10 and further branch to a respective one of the distribution microchannels k3*l*. Thus, a node k20 may potentially ensure fluidic communication from the input microchannel to the distribution microchannel it branches to. Note that the converse does not necessarily hold as nodes are preferably unidirectional.

For example, m=4 in FIG. 1, which depicts four microfluidic modules 141-144, respectively connected by four distribution channels 131-134. The four microfluidic modules 141-144 further connect to four output channels 111-114, respectively. FIG. 1 otherwise show an upper (horizontal) set of m nodes, which branch, each, from the input channel 110 and branch into respective distribution channels 131-134. Because the present devices typically include additional sets of nodes, the upper, horizontal set of nodes is referred to as a "first set" of nodes in the following. As further illustrated in FIGS. 1-3, the input microchannel k10 may for instance include m junctions 110J and each of the m nodes may branch from the input microchannel 110 at a respective one of the m junctions 110J.

A node may include various elements, such as, e.g., an inlet port (or an inlet channel), a cavity, a liquid pinning feature, a via, and one or more outlet ports, as discussed later in reference to FIGS. 2-3 and 7C, 7D. For example, different types of nodes may be contemplated, which may be altered so as to modulate the fluidic connection.

Thus, the present devices can be functionalized (and so customized) by altering some of their nodes. After functionalization, a subset, but not all, of the nodes k20 are altered, compared with remaining nodes of the set. Due to this alteration, the nodes k20 exhibit different liquid pinning strengths. As a result, the extent in which a liquid introduced in the input microchannel k10 will reach one or more of the m microfluidic modules k4*l* varies and, this, according to the different liquid pinning strengths of the nodes, in operation.

Thus, the extent in which a node effectively allows a liquid to pass from the input microchannel to a downstream module depends on the alteration state of that node. That the liquid pinning strengths of the nodes be alterable means that the device is configurable. In other words, the fact that nodes can be altered allows the microfluidic circuit to be configured based on the alteration states of the nodes. As a result, the downstream microfluidic modules k4*l* may be contacted (i.e., wetted by liquid introduced in the input microchannel), e.g., after a certain period, or even not at all, depending on the pinning strengths of the nodes.

This, as one understands, allows a microfluidic device to be programmed. Incidentally, preferred embodiments of the invention make it possible for nodes to be altered during a final stage of fabrication, or even to be re-configured (so as for the device to be re-programmable). Thus, at an intermediate stage of fabrication, none of the nodes of the device may be altered yet. Yet, we keep in mind that if none of the nodes are altered or if the nodes are all altered in a similar way, then the nodes typically have all the same liquid pinning strength and no specific functionalization of the device is obtained. Rather, programming the device typically results in that only a subset of the nodes are altered (or at least the nodes are not all altered in a same way), in order to differentiate liquid dynamics through the modules and, thus, functionalize and customize the microfluidic device.

In simplest embodiments, the nodes are altered to act in a binary fashion, i.e., as switches that let pass the liquid, or not. In that case, the microfluidic nodes can be compared to transistor switches or logic gates. Namely, the nodes k20 may be configured so as to either pin a liquid thereat or let a liquid pass there-through. Also, a node may be designed to be "normally ON" (and hence need be altered to become OFF) or, conversely, a node may be designed to be "normally OFF" and be altered to become OFF. In variants, the nodes k20 may be altered so as to enable distinct flow rates of liquid there-through, so as for liquid to effectively reach the modules at different times.

In addition, the present microfluidic circuits may be hardcoded, i.e., with the nodes altered in a non-reconfigurable way. However, in embodiments, the microfluidic devices may be reconfigurable, at least partly.

In the context of this invention, one may ideally want to enable a complex microfluidic circuit, e.g., including a plurality of functionally distinct modules, and allow the device to be programmed so as to enable any fluidic sequence throughout the modules. This, however, may typically result in a very complex architecture and large device footprints. Thus, it is of remarkable advantage to rely on a crossbar switch-like configuration of the nodes. Not only this allows to reduce the footprint of the devices but, in addition, this eases the programming of the nodes. To achieve this, best is to rely on transverse sets of input/output channels and distribution microchannels. Transverse channels here mean non-parallel channels, arranged on distinct levels of the device, i.e., channels whose respective projections on an average plane of the device are transverse.

Now, to make this possible, one may advantageously rely on a multilevel device, such as depicted in FIGS. 1, 5-7, wherein the different sets of microchannels are provided on distinct levels of the device. Furthermore, in order to interconnect the channels, one preferably rely on 3D nodes, e.g., having inlet and outlet on distinct levels in the device, as described below in reference to FIGS. 2, 3 and 7.

This way, complex architectures of non-parallel microchannels can be achieved, which are configurable (and possibly re-configurable) and, this, based on a same initial microfluidic template. Once customized, only a subset of the microfluidic modules will typically be or remain activated. More generally, the different modules may be activated at different times, it being noted that de-activated or non-activated modules can be regarded as modules that are activated at an infinite time period after a liquid was initially introduced in the input microchannel. Otherwise put, the time at which a module is activated (i.e., reached by liquid) depends on the liquid pinning strengths of nodes connected thereto.

In addition, the modules may possibly be linked, so as to enable sequences involving a given order of modules that will be reached by a liquid. For example, a same input flow may reach a given one of the module after another, given one of the modules, etc.

This, as it may be realized, has considerable advantages in terms of manufacture, inasmuch as a multi-purpose microfluidic device template may be designed, which potentially enables multiple applications (e.g., fluid reaction, fluid mixing, optical detection, etc.), for which only a subset of the modules need be activated and, possibly, according to a given timing and/or a given order. This is achieved thanks to suitable node architectures and suitably altered nodes, as proposed in embodiments herein. Finally, as a same, multi-purpose microfluidic device template can be designed and mass-fabricated, considerable cost-saving can be contemplated.

In embodiments, the microfluidic device k includes m additional sets of m nodes k20 each, in addition to a first set of m nodes k20, so as to potentially allow liquid to pass through given ordered pairs of modules. In each of the examples of FIGS. 1, 4, 8 and 9, the first set of m nodes corresponds to the upper, horizontal set of nodes branching from the input microchannel k10. Moreover, m additional sets of m nodes k20 each are provided below the upper set (with m=4 in FIGS. 1, 4 and 8 and m=8 in FIG. 9).

Such a device k further includes a set of m output microchannels k1$l$ (l=1, . . . , m), each connected to an output of a respective one of the m microfluidic modules k4$l$. The m output microchannels are associated to the m additional sets of nodes. That is, each of the m output microchannels k1$l$ branches into each of the m nodes k20 of a respective one of the m additional sets. Furthermore, each node of each additional set branches to a respective one of the distribution microchannels k3$l$. In other words, each node of each additional set connects an output channel k1$l$ to a distribution channel k3$l$.

For example, in FIG. 1, the first node in output of the upper module 141 connects to the first distribution channel 131, which connects to the same module 141. The second node in output of module 141 connects to the second distribution channel 132, and so on. For example, the $l^{th}$ node connects to the $l^{th}$ distribution channel. A similar configuration is assumed in FIGS. 8 and 9 (although the lower channels are hidden in FIG. 9). As seen in these examples, the distribution channels are preferably nested, to reduce the footprint.

Now, the additional nodes may be altered, so as to exhibit different pinning strengths. For instance, a subset (not all) of the m nodes of at least one of the m additional sets may be altered, compared with remaining nodes of this set, so as for the nodes of this set to have different liquid pinning strengths. As a result, liquid introduced in the input microchannel k10 (at an initial time) passes through at least one ordered pair of the m microfluidic modules k4$l$. The sequence actually enabled is here determined by the different liquid pinning strengths of the nodes of: (i) the first set of m nodes; and (ii) said at least one of the m additional sets, in operation. Of course, nodes in other ones of the additional sets may be altered too, to enable more complex sequences.

In embodiments such as depicted in FIGS. 1, 4, 8, 9, the device each time includes m+1 sets of m nodes k20 each, in total, including the first set of m nodes. There are thus m×(m+1) programmable nodes in total in such cases. Again, such nodes are preferably configured so as to either pin a liquid or let it pass.

As for instance seen in FIG. 1, each output microchannel 11$l$ (l=1, . . . , m) includes m junctions 11$l$J. Each additional set of m nodes branches from a given one of the output microchannels 11$l$ at the level of a respective junction. That is, each node of any one of the additional sets branches from a given one of the output microchannels, at a respective one of the m junctions 11$l$J. A similar configuration is adopted in each of the devices of FIGS. 4-8.

Since each node of each of the m additional sets branches to a respective one of the distribution microchannels k3$l$, the nodes may, as a whole, potentially allow fluidic communication between $m^2$ ordered pairs of the microfluidic modules k4$l$, subject to comments below.

The $m^2$ ordered pairs that can potentially be enabled stem from the fact that the input microchannel branches into each of the m nodes of the first set, thus giving m possibilities for the first module (i.e., the first element of the ordered pairs). Now, the output microchannel of any module branches into each of the m nodes of a respective one of the additional sets, yielding m possibilities for the second element of the ordered pairs and, this, for each of the m first elements. There are thus potentially $m^2$ ordered pairs of modules than can be put in fluidic communication (which can be regarded as an arrangement with repetition, as to the number of 2-tuples of an m-set).

Now, the additional nodes may further be configured to allow a number of sequences of modules. A sequence corresponds to an ordered n-tuples of modules). Yet, the number of arrangements of fluidic sequences that are effectively enabled in practice is typically (much) smaller. Indeed, each set of nodes will typically be programmed to allow liquid passing therethrough to reach a reduced subset of the modules (typically, at most one module). In addition, and depending on the precise structures of the node and distribution channels, it may physically be impossible for liquid exhausted by a given module to later re-enter that same module, despite the presence of an interconnecting node, due to the presence of liquid in the corresponding distribution channel.

Assuming, for instance, that liquid exhausted by one module should at most reach a distinct module (which was not used so far, such that liquid never passes twice through a same module), there are m possibilities for the first module to be reached by liquid, m−1 possibilities for the second, etc., such that there are m! possibilities of fluidic sequences in total. Yet, not all of the modules need be exploited in practice, such that much simpler sequences will typically be enabled.

For example, assume that one pair of modules is effectively needed, e.g., one for reaction purposes, and another one for detection purposes. In that case, a single node need be activated in the first set (i.e., the upper set in FIG. 1), in order to allow liquid to reach the reaction module. Next, a single node need be activated in output of the reaction module, to allow liquid to reach the detection module.

Figure 4:
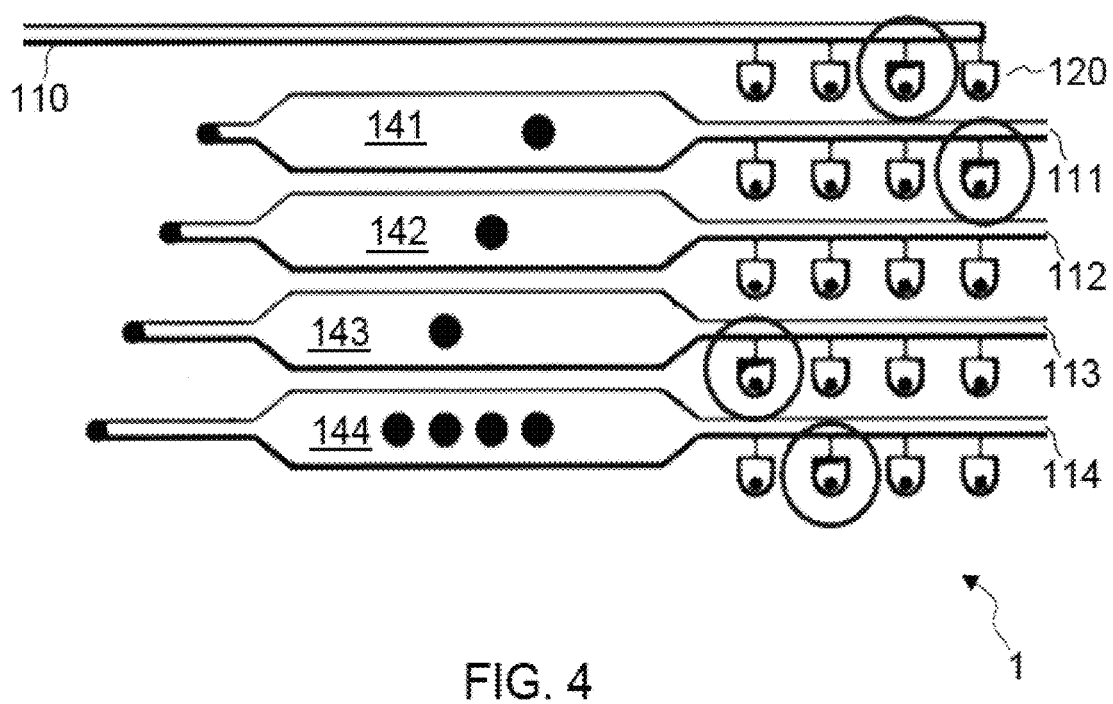
FIG. 4 is a photograph (in gray level, highly contrasted for depiction purposes) of a top view of a prototype device, having a configuration as shown in FIG. 1, whose activated nodes are emphasized.

As another example, FIG. 4 shows a photograph of the top layer of actual microfluidic device (which has the same configuration as the device of FIG. 1), wherein activated nodes are emphasized. The sequence enabled is as follows:

The $3^{rd}$ node of the upper set of nodes is activated, which enables fluidic connection to the third distribution channel (not visible in FIG. 4, corresponding to channel 133 in FIG. 1) and thus brings liquid to the third module 143, in operation. Liquid exhausted from this module 143 reaches the output channel 113 and, in turn, the $3^{rd}$ additional set of nodes that branch therefrom;

In the $3^{rd}$ additional set of nodes (i.e., the $4^{th}$ set starting counting from the top): only the $1^{st}$ node is activated, which brings liquid to the first module 141, then to output channel 111 and the $1^{st}$ additional set of nodes; and In the $1^{st}$ additional set (underneath the upper set): only the $4^{th}$ node is activated, which brings liquid to the $4^{th}$ module 144;

In the $4^{th}$ additional set: only the $2^{nd}$ node is activated, for liquid to reach the $2^{nd}$ module 142; and None of the nodes is logically activated in the $2^{nd}$ additional set, in output of the second module 142, as this module is the last to be reached by liquid.

Accordingly, liquid initially introduced in the input channel 110 successively passes through the third module, the first module, the fourth module and finally the second module. A particular sequence of four distinct modules is effectively enabled in that case and all the modules are effectively exploited here. In variants, only a subset of the modules could have been exploited and, possibly, in a different order. Note that, in the example of FIG. 4, most nodes are not activated and a distribution channel is at most activated once (the lth node in any set is at most activated once), to avoid short-circuits.

Now, we note that the design of the device and the operation may make it physically impossible for liquid to re-enter a same module, even if the interconnecting node is activated. For example, the design assumed in FIGS. 1-3 prevents this. Assume that module 141 is enabled, as per activation of the first node in the upper set (call it the first activated node). Now, even if the first node in output of module 141 is activated (called second activated node), so as to tentatively allow liquid to re-enter module 141 via the first distribution channel 131, liquid that already fills channel 131 due to the as per the first activated node prevents additional liquid insertion from the second activated node, especially as constriction valves are provided in channel 131 in this example. Thus device may be configured such as to prevent liquid short-circuits. Yet, if liquid has already left the channel 131 at the moment a liquid front re-enters channel 131, then it may be possible for liquid to re-enter a same module. This, however, requires precise control on liquid segments.

Whether liquid short-circuits are permitted or not depends on the exact structures of the nodes and the distribution channels, e.g., on the possible presence of vents, valves, etc. Of note is that liquid short-circuits may advantageously be exploited to cause to block liquid in a given module. This can be useful in some cases, e.g., for detection purposes. Incidentally, creating short-circuits is typically not an issue in devices implemented on wicking media, since the porosity of the latter allow for venting intrinsically.

Thus, in general, the present devices may allow a module to branch into any of the modules (i.e., another module or, even, that same module), even though short-circuits may be avoided, by suitably programming the nodes, or prevented, due to the residual liquid in the distribution channels and the configuration of the device.

Now, in typical scenarios, short-circuits are not needed. Rather, the device is typically configured for a given module to effectively branch into a distinct module that is not meant to be activated before said given module, as in the scenario of FIG. 4. In other words, the device is typically configured (i.e., programmed) so as to allow a sequence of modules to be successively reached by liquid. This reflects in that each distribution channel is at most activated once, which precludes potential issues in terms of liquid short-circuits.

To summarize, devices such as depicted in FIGS. 1-9 allow a liquid introduced in the input microchannel k10 at an initial time to pass through one or more ordered pairs. Thus, liquid may pass through a sequence of distinct modules k4l, wherein a sequence chains up ordered pairs of microfluidic modules k4l. In all cases, the actual liquid paths depend on the alteration states of the m×(m+1) nodes. Again, one understands that such embodiments literally allow the microfluidic modules to be programmed.

As noted earlier, the nodes k20 are preferably configured so as to either pin a liquid or let it pass, i.e., to effectively act as an OFF-ON switch. Preferably, the microfluidic nodes of each of the present device are all functionally similar, if not all identical (as assumed in the appended drawings), whether they belong to the first (upper) set or the additional sets of nodes. This simplifies the design and programming of the device. Now, variants can be contemplated, in which the nodes are differentiated. I.e., some of the node may effectively act as a binary switch, whereas other nodes may more subtly be configured to allow different flow rates of liquids passing therethrough, to give rise to complex liquid sequences. In addition, a node may have two (or more) outlet ports, as in FIG. 10, such that a module may effectively branch into two subsequent modules and, this, via a single interconnecting node. As one understands, many variants can hence be contemplated.

As illustrated in FIGS. 1, 4-9, the present microfluidic devices k preferably involve nodes in a crossbar switch configuration. That is, such devices include m+1 sets of m nodes k20, which are arranged as an array of m×(m+1) nodes, intercalated between an inlet channel and an outlet channel, in a crossbar switch configuration. I.e., this array is preferably rectangular, so as to form an array of m+1 recognizable rows of m nodes each, forming m columns, as in the examples of FIGS. 1 and 4-9. Each node of this array branches from a horizontal channel into a vertical channel, just like electronic crossbar switches include switches at each intersection of a crossed pattern of interconnecting lines. Relying on such an array eases the design of the device and further makes it more easily programmable.

Now, in the examples of FIGS. 1-3, the m additional sets of nodes k20 and the distribution microchannels normally prevent liquid exhausted by a given one of the modules k4l to later re-enter that same module, assuming liquid is continuously fed in the input channel k10, as noted earlier. Yet, this has little consequences in practice as a microfluidic module is typically meant to be used once. Thus, in a crossbar switch configuration, wherein nodes act as ON-OFF switches (as assumed in FIG. 1 or 4), this means that diagonal nodes have little use in practice and could simply be omitted.

Therefore, embodiments can be contemplated, which involve a crossbar configuration of $m \times (m+1) - m = m^2$ (i.e., diagonal nodes are skipped).

Similarly, some node connections may be excluded ex-ante, because of particular design options, e.g., because it does not make sense, practically, to potentially connect specific pairs of modules. In that respect, the microfluidic modules will typically have different functions. The set of microfluidic modules may notably include one or more of: an optical detection chamber (configured in the device so as to enable optical detection); a fluid mixing chamber; and a reaction chamber. The present devices include at least two modules and, more likely, they may include 3, 4, 8 or even more modules.

Figure 9:
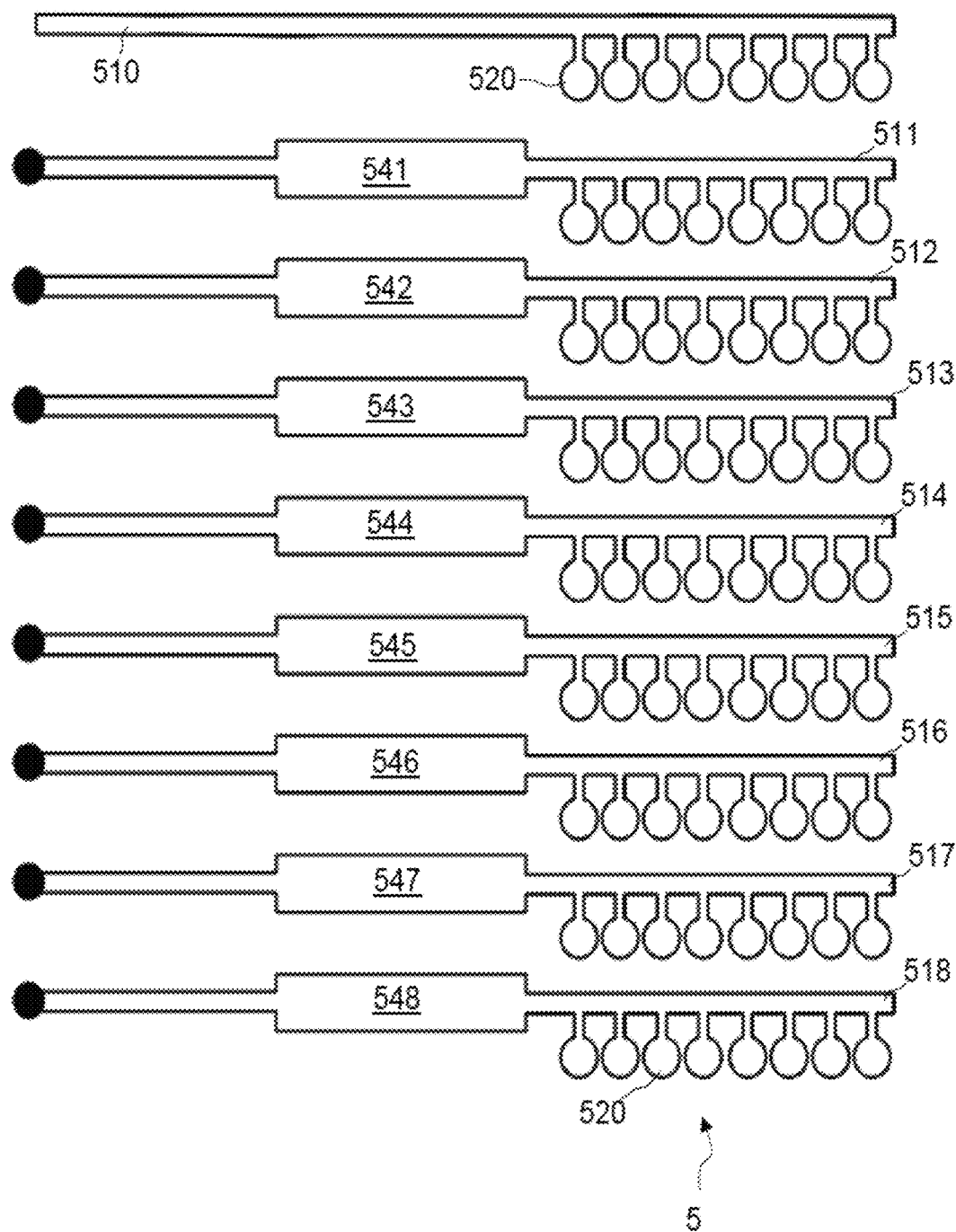
FIG. 9 is a top view of another microfluidic device, comprising eight microfluidic modules, connected in a crossbar switch configuration, as involved in embodiments.

Consider for instance the microfluidic template of FIG. 9, which includes eight distinct modules. The design of FIG. 9 is an attempt to a "universal" microfluidic platform, which involves (from top to bottom) three orthogonal flow mixers 541-543 (e.g., as disclosed in US 20160279632 A1), two microfluidic reaction chambers 544-545 (as known per se), a mixer 546 (as known per se) and two detection modules 547-548 (as also known per se). Such a chip may be configured during the reagent integration step by selecting which components will be used. This chip template can for instance be configured to implement multiplexed assays, multistep reactions, etc.

For optical detection purposes, one side of the device (on which the modules are) is preferably covered by a light permissive (e.g., transparent) cover or lid. However, the nodes may be concealed (not under a transparent window). This way, a user cannot guess which of the modules are activated upon visual inspection. Similarly, the back (distribution) channels may be concealed.

As seen in the example of FIG. 9, some of the modules may have a similar function, such as detection modules 547-548. Now, some connection may be excluded by design (e.g., it may not be necessary to potentially connect two detection chambers). More generally, it may not be necessary to potentially connect all pairs of modules. In that case, the additional set of nodes may include less than m nodes each. For example, the device may include m additional sets of m−1 nodes each, be it to exclude short-circuits, as noted earlier. More generally, only specific pairs may potentially be connected by nodes.

Thus, and according to another aspect, the present microfluidic devices may be embodied as a device that includes, a minima, at least two microfluidic modules and, consistently, a first set of at least two nodes (each connecting the input microchannel to a respective one of the modules), as well as a second set of at least two nodes. Said "second set" corresponds to the superset formed by m additional sets of a reduced number (<m) of nodes, compared with the m×(m+1) node configurations described earlier. Nodes in the second set potentially connect ordered pairs of distinct modules. Now, consistently with earlier embodiments, a subset of the nodes of each of the first set and the second set may be altered, so as for the nodes to have different liquid pinning strengths, in each of the first and second sets. As a result, liquid introduced in the input microchannel passes through at least one ordered pair of two microfluidic modules. The sequence actually enabled is again determined by the different liquid pinning strengths of the nodes of each of the first set and the second set.

However, and as the present Inventors observed, reducing the number of potential connections does not happen to simplify the design of the devices in practice, contrary to what one would expect. In fact, this even challenges the concept of universal microfluidic chip. Eventually, it is perhaps simpler to adopt a design with m×(m+1) nodes, in a crossbar switch configuration. In addition, a m×(m+1) crossbar configuration may allow more flexibility, inasmuch as one may want to exploit short-circuits and hence stop liquid flow in one or more modules, e.g., for detection purposes, as noted earlier.

As illustrated in FIGS. 1-3, 7, the components of the present microfluidic devices k are preferably arranged according to distinct, parallel levels of the device. A level is a subdivision of the device, i.e., a section parallel to the main plane. Assuming the microfluidic device is approximately a parallelepiped volume, then a given level can be regarded as a parallelepiped section of that volume. That is, if the device has N levels (N=2, 3, . . . ), then the device can be regarded as fitting in a parallelepiped bounding box of height h, which can be partitioned into N contiguous parallelepiped volume sections of height $h_i$, such that $\Sigma h_i = h$. Components of this device will then essentially extend in one or the other of these volume sections.

Figure 2:
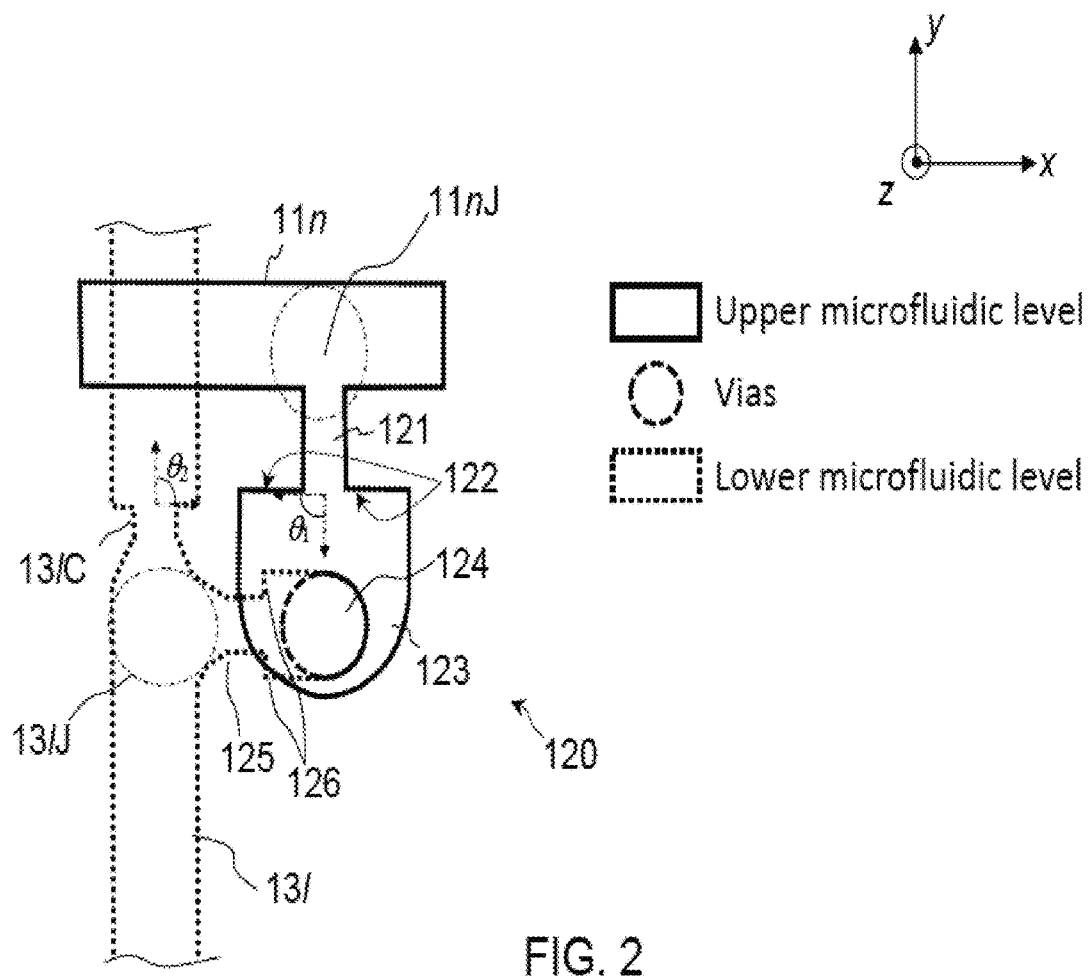
FIG. 2 and FIG. 3 shows a top view of a 3D node, which can advantageously be used in the device of FIG. 1, as in embodiments. This node comprises liquid pinning structures, which may be foiled thanks to wetting material judiciously placed in the cavity of the node, as illustrated in FIG. 3, so as to activate the node.
Figure 3:
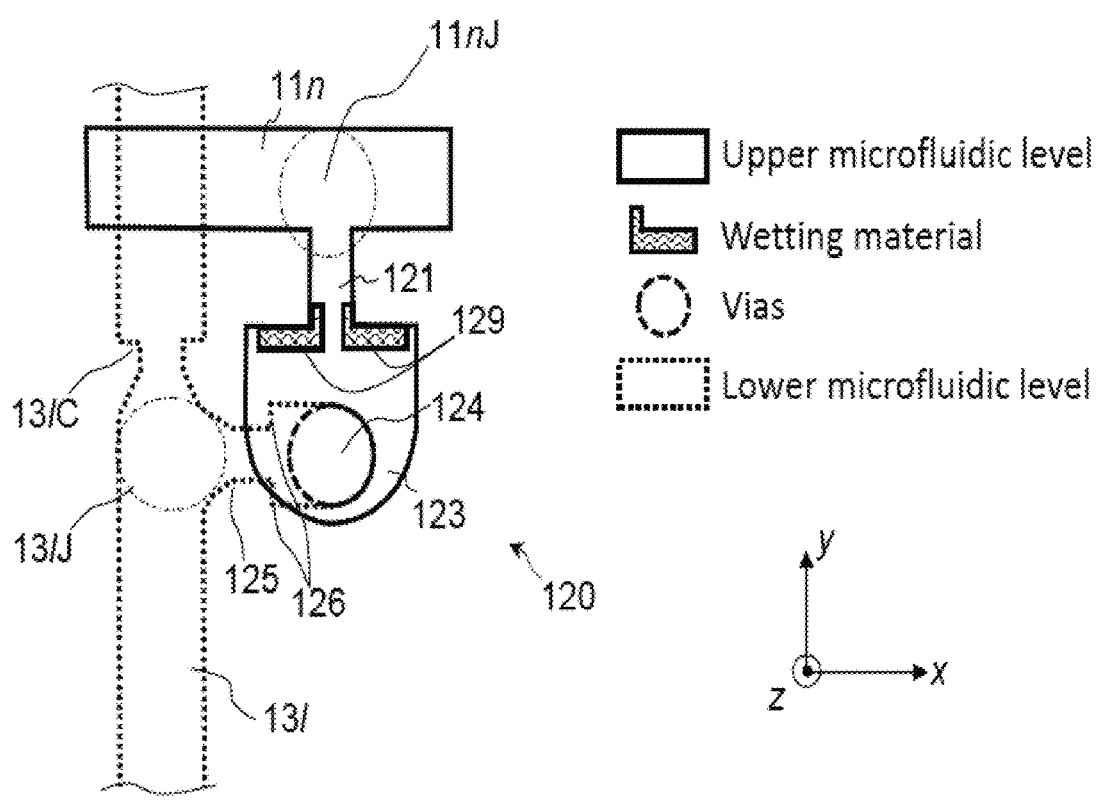

As for instance suggested by the patterns of dashed and dotted lines of FIGS. 1-3, the input microchannel 110 and the output microchannels 11l may be defined on a first (top) level of the device, whereas the distribution microchannels 13l are defined on a second (bottom) level. Each level may be embodied by a respective layer, or by several layers, as discussed later in reference to FIGS. 5-7. In addition, an intermediate level (or layer) is preferably involved, between the first and second levels (layers), for reasons explained below. These arrangements allow transverse, 3D channel configurations, where, e.g., both the input channel and the output channels are arranged parallel to a first direction, on a first level, whereas the distribution channels are arranged parallel to a second direction (transverse to the first direction), on a second level. Such transverse channel configurations allow more compacts arrangements of the channels to be designed and, in turn, devices of reduced footprints to be achieved. Transverse channel configurations are particularly desired in embodiments relying on crossbar switch configurations of the nodes.

Now, 3D nodes may advantageously be relied upon, so as to enable transverse, 3D channel configurations as evoked earlier. For example, referring to FIGS. 2, 3, 7C and 7D, some or (preferably) all of the nodes k20 of the m+1 sets of m nodes include, each: an inlet port; a cavity; a via; and an outlet port.

As seen in FIG. 2, 3 or 7C and 7D, the cavity k23 of each node k20 of a device k may be formed on the first level of the device, with the cavity k23 open on top. The inlet port k21 is also formed on the first level of the device. The inlet port k21 branches from the input microchannel k10 (or one of the output microchannels k1*l*) and communicates with the cavity k23 through an ingress thereof. The outlet port k25 branches to one of the distribution microchannels k3*l* on the second level. Next, a via k24 extends from the cavity k23 to the outlet port k21, so as for the cavity k23 to communicate with the outlet port k25. The via k24 typically extends perpendicular to a mid-plane of the first and second levels, i.e., in an intermediate level between the first and second levels of the device. The outlet port k25 may have a rather complex structure (as in FIGS. 2, 3 and 10) or, in variants, be defined as a mere orifice delimiting a lower portion of the via k24 (as in FIGS. 7A-7D).

In addition, the cavity k23 includes or is otherwise closed off by a liquid blocking element k22. This element is generally configured to prevent an aqueous liquid that fills the inlet port k21 to reach the outlet port k25 of the node.

That the cavity k23 be open on top makes it easy to fabricate; it is for instance sufficient to etch the cavity 123 and the input microchannel 110 (FIGS. 1-3) in the upper thickness of a silicon (Si) substrate, as in the example of FIG. 1. Plus, this makes the cavity easily accessible from the top, which eases operations needed to alter the blocking element. One may for instance spot a wetting material 129 or remove (or otherwise alter) the liquid blocking element 122 from the top (before covering the device), to reduce the pinning strength of the node. If a mere binary switch is desired, the blocking element may be altered so as to merely activate the cavity 123 and enable liquid circulation therethrough. Eventually, this allows an aqueous liquid to enter the cavity k23 and then reach the outlet port k25 of the node k20.

This way, an alterable (e.g., activable or deactivable), multi-level node is achieved, which allows a 3D microfluidic circuit to be configured (and possibly re-configured) based on the alteration state of the blocking element(s) of the cavity k23. The 3D configuration of the node makes it suited for use in a multi-level circuit that includes transverse channels, as in FIG. 1 or 8.

Figure 10:
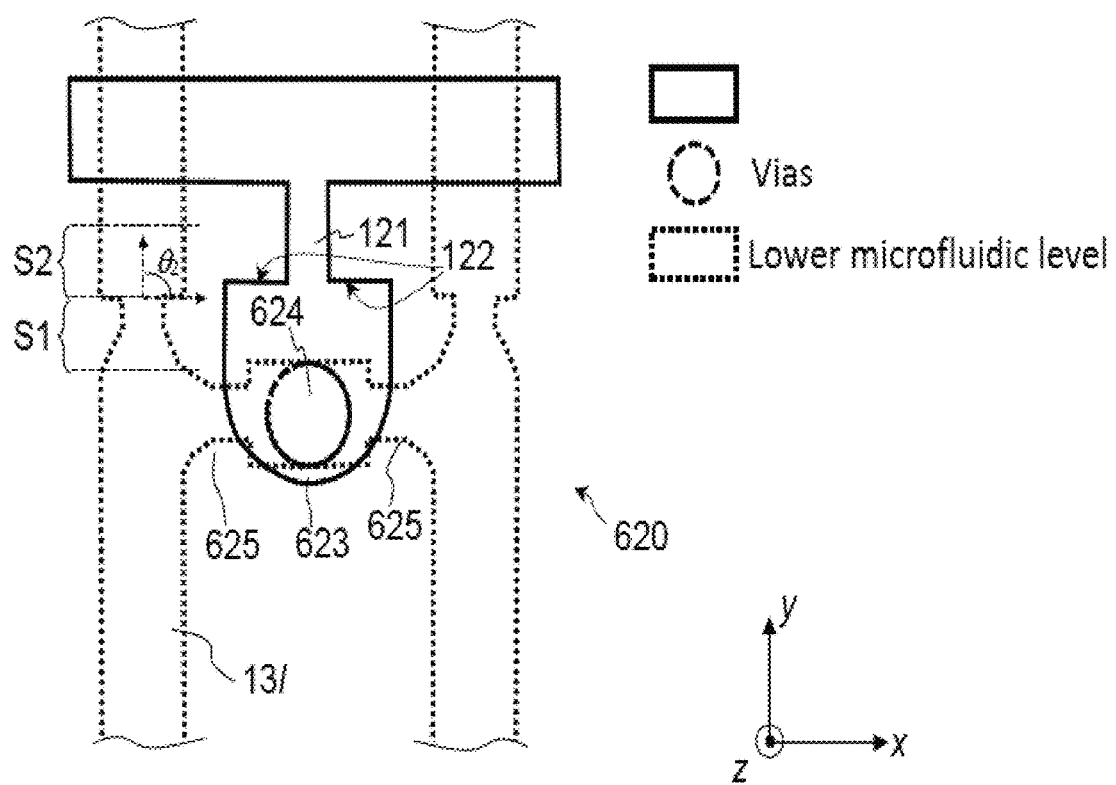
FIG. 10 is a top view of a variant to the node of FIG. 2, wherein the node branches into two distribution channels, as involved in embodiments.

For simplicity, one node typically has one input port and one output port only, as in the examples of FIGS. 1-9. However, more sophisticated variants may be contemplated, where one node has, for example, two output ports, as illustrated in FIG. 10. In that case, a single node activation allows two modules to be concurrently activated.

As further assumed in FIGS. 2-9, the via k24 preferably extends on an intermediate level of the device, between the first level and the second level. The via further extends from a bottom side of the cavity k23 (opposite to the top side) down to the outlet port k25. Such a design eases the fabrication of a device with transverse channels. Indeed, it suffices to open the vias from the bottom side of the cavities. Meanwhile, imposing an intermediate level between outer levels eases the design of devices with transverse channels as this intermediate level prevents short-circuits between the transverse channels. That is, the intermediate level extends between outer levels on which the channels k10, k1*l* and k3*l* are provided. Since the transverse channels are typically open on top of their respective levels (they can for instance be etched, grooved or otherwise formed on the upper thicknesses of a material layer), the intermediate level makes it possible to close the channels defined on a lower level and prevent short-circuits with channels defined on the upper level.

A node structure such as described above is easily duplicable and, thus, a plurality of such nodes may easily be obtained, which are particularly suited for implementation in a crossbar switch configuration, together with non-parallel channels on distinct levels of the device. Eventually, such nodes allow, together with a transverse channel configuration, the footprint of the devices to be reduced.

In embodiments such as depicted in FIGS. 1-3 and 10, the liquid blocking element is a pinning structure 122 formed at the ingress of the cavity 123. The pinning structure 122 is configured to stop (or at least challenge the progression of) a liquid filling front of an aqueous liquid at the ingress of the cavity 123. This makes it particularly simple to activate the cavity. Indeed, as the pinning feature 122 is arranged right at the ingress of the cavity, the room left vacant in the cavity can conveniently be exploited to spot a wetting material 129 or otherwise alter the pinning structure 122, in order to alter the pinning strength of the node. The pinning structures is typically altered from the top. Still, the device may be sealed, at a later stage, e.g., by covering all open structures on top with a lid, as usual in the art.

As illustrated in FIG. 2, 3 or 11, the liquid pinning structure 122 is preferably formed by an opening angle $\theta_1$ of the cavity 123, which angle is preferably between 90° and 160°. Yet, this angle may be between 60° and 90°, provided hydrophobic walls are used, as explained earlier. This opening angle is measured between an average flow direction of liquid at the input port (i.e., along −y) and one or more walls of the cavity 123 around the ingress, wherein such walls extend in a plane parallel to (x, z), as seen in FIG. 2. For example, this angle may be of 90°, i.e., formed by a straight wall (extending perpendicularly to the liquid inlet direction −y), to which the inlet port leads.

In more sophisticated embodiments, this angle is strictly larger than 90° (e.g., it is between 110° and 160°). In all cases, considering a situation where liquid fills the inlet port with an advancing contact angle, the enlargement, i.e., the widening at the entrance in the cavity adds an angle component that challenges the propagation of the meniscus into the cavity. A particularly satisfactory value for this angle is 135°.

In the examples of FIGS. 2, 3 and 10, the ingress of the cavity 123 further has a width (as measured along axis x) that is smaller than the depth (measured along z). Walls of the cavity, on each side of the ingress, are separated by a gap corresponding to the width of the ingress. Said walls accordingly form two opposite opening angles $\theta_1$ in the cavity, where each angle is between 60° and 160°. The inlet port 121 may for instance extend along a main axis of the cavity 123 (parallel to axis y), so as for the ingress to be centered in the cavity. This way, two lateral edges 122 are formed on each side of the gap, which, in turn, yields the two opening angles $\theta_1$. Since, in addition, the depth of the ingress is larger than the width, liquid that gets laterally pinned at the ingress of the cavity cannot overcome the pinning barrier by capillarity, i.e., by wetting both a bottom of the inlet port and cavity and an opposite lid, in operation.

Best is to have the ingress centered at the entrance of the cavity 123. Yet, in variants, the ingress may be off-centered, laterally (along x), a thing that may lead to partial liquid pinning only. In other variants, other pinning structures may be involved (such as pillars or other microfluidic structures) to pin the liquid.

As illustrated in FIG. 3, the node of FIG. 2 may easily be altered, e.g., thanks to a wetting material 129 spotted at the liquid pinning structures 122. This wetting material allows an aqueous liquid filling the inlet port 121 to reach the outlet port 125, notwithstanding the liquid pinning structure 122, in operation. The wetting material 129 may for instance include wetting chemicals, spotted at the locations of the pinning structures 122, or wetting micro-particles, a liquid, a dye, salt, or a surfactant. More generally, this could be any material whose residual material (once dried) is wettable by an aqueous liquid such as water or an aqueous solution.

In variants, the liquid pinning structures 122 may be physically altered (instead of chemically), in order to allow the liquid to reach the outlet port 125. For example, the opposite ingress edges 122 of the cavity may be physically altered to smooth the opening angles, such that a liquid filling front may pass the ingress and wet the cavity 123. This, however, typically makes it more difficult to configure the nodes.

In the example of FIGS. 2, 3 and 10, the cavity is disabled, by default (i.e., normally OFF). Only those nodes that need be activated (to enable the desired ordered pairs of modules) will be altered in that case, which is simply achieved thanks to cavities that are open on top (before sealing).

In embodiments such as depicted in FIG. 1-3, the inlet ports 121 of nodes of a same (e.g., horizontal) set 120 of nodes may have different hydraulic resistances. The width of the inlet port 121 and so the ingress of the cavity impacts the pinning strength of the node. Having inlet ports of different hydraulic resistances may thus be exploited to compensate for the differences in flow rates of liquid reaching the shifted inlet ports of nodes of a same set, whether branching from the input channel 110 or any of the output channels 11l. For example, the width and/or the length of the inlet ports 121 may be varied, as the hydraulic resistance notably depends on the geometry of the conduits.

As further illustrated in FIGS. 2, 3 and 11, the outlet ports 125 of the nodes 120 may optionally include a fluid flow constriction valve 126, so as to prevent an aqueous liquid in the distribution microchannel 13l branched by the outlet port 125 to reach the via 124. This valve 126 is provided to prevent liquid in the distribution channel to enter this node. I.e., the pinning strength of the valve 126 of the outlet port 125 depends on the flow direction. For an incoming flow, it has a higher pinning strength than the portion of the microchannel 13l at the level of the junction 131J, at which the outlet port 126 branches. The valve 126 may for instance form two opposite opening angles for a liquid flow coming from the branched distribution channel 13l, just like the liquid pinning structures 122 at the ingress of the cavity.

As seen in FIG. 2 or 3, the output port 125 branches to a distribution channel 13l, at the level of a junction 13lJ, which preferably includes a fluid flow constriction valve 13lC, on one side of this junction 13lJ. This additional valve forces an aqueous liquid exhausted through the outlet port 125 toward direction −y. However, and as seen in FIG. 2, an aqueous liquid coming from the other side of the junction may pass the valve 131C. Thus, the outlet port 125 and the valve 13lC of the second microchannel 13l function as a diode. This makes it possible for a column of nodes to branch to a same distribution microchannel. Meanwhile, the valve 126 prevents liquid already present in that column (that possibly comes from higher, activated nodes) to enter the node.

In embodiments, the fluid flow constriction valve 131C is formed by differently shaped sections S1, S2 of the channel 13l, as depicted in FIG. 10. The first section Si is tapered and leads to the second section S2, which has a larger average diameter than the first section, so as to provide an opening angle $\theta_2$ in the second section, which again may be between 60° and 160°. The opening angle $\theta_2$ is measured between a main longitudinal axis of the outlet channel 13l (parallel toy) about the constriction valve and one or more walls of the second section S2, to which the tapered section Si leads. Thus, a liquid flow coming from the first section Si is pinned at the ingress of the second section S2, whereas liquid flow coming from the opposite direction can pass the constriction 13lC.

Figure 5:
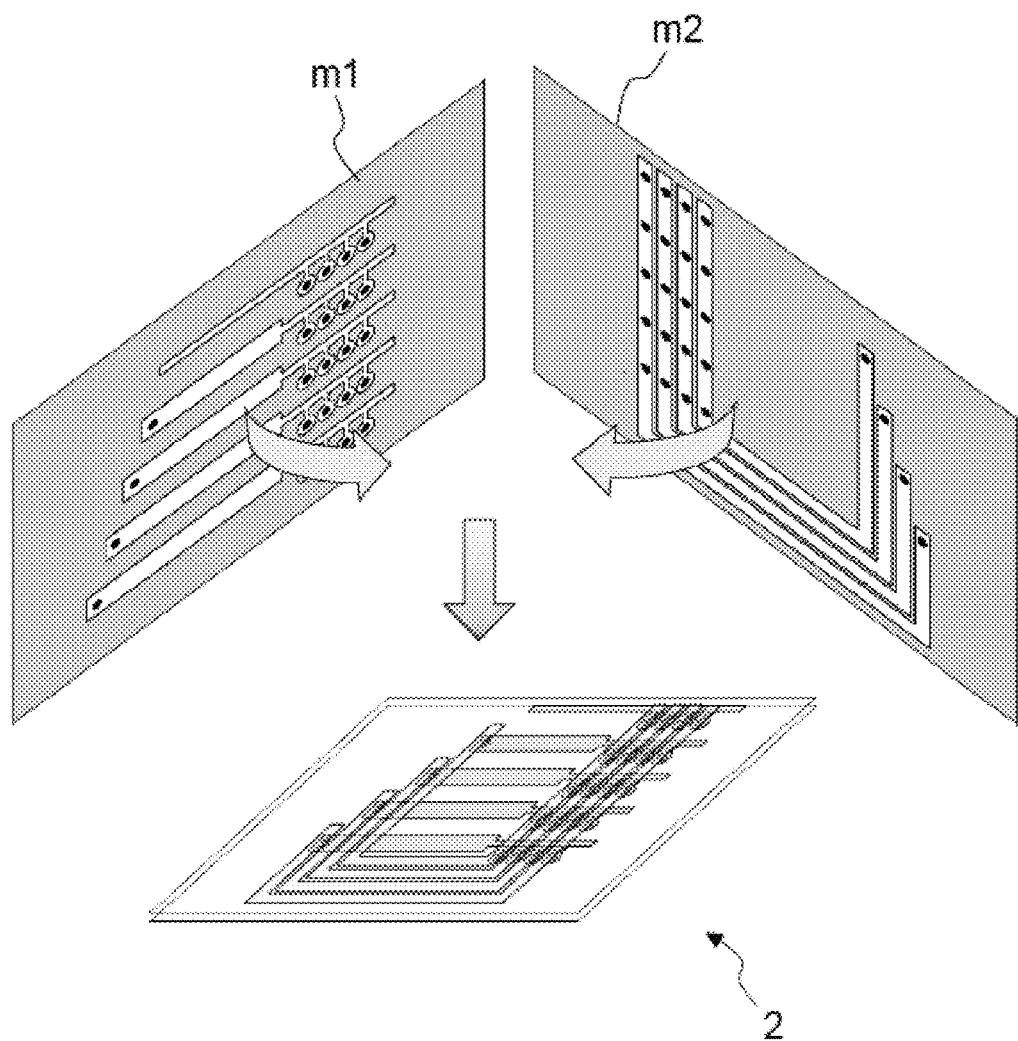
FIG. 5 and FIG. 6 are 3D views illustrating possible fabrication methods of present microfluidic devices, relying on injection molding techniques.
Figure 6:
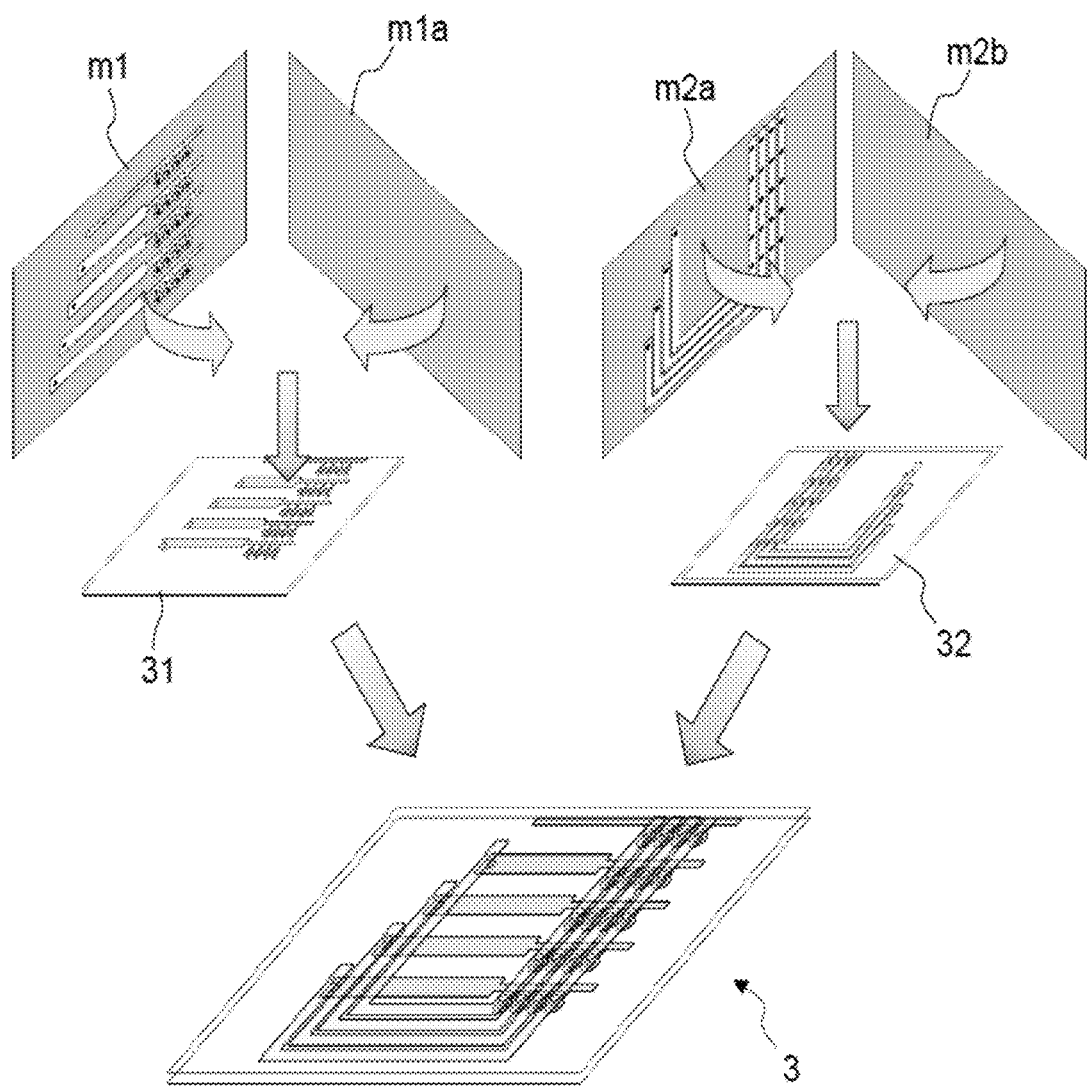

FIG. 1 assumes microfluidic structures etched in silicon chips. In other embodiments, polymeric chips may be fabricated using injection molding techniques, as illustrated in FIGS. 5 and 6. In still other embodiments, wicking media may be used as a basis to form the various flow paths needed, as assumed in FIGS. 7A-D.

FIGS. 1 and 4 depict a 3D microfluidic chip fabricated in silicon, and comprising four microfluidic modules (i.e., empty chambers in that case, though black food dyes have been deposited, for visibility purposes in FIG. 4). Channels are patterned on each side of the core silicon chip, which include: an input channel 110, the modules 141-144 and four output channels 111-114 on one side; and four distribution channels 131-134 on the other side. Through vias 124, 131V-134V ensure fluidic communication from one side to the other. Twenty routing nodes are intercalated to provide complete control over the flow paths. The flow path surfaces can for instance be silanized (trichloro(octyl)silane), to achieve wetting surfaces. The microchannel depths is of about 20 μm. The microfluidic structures are covered by PDMS covers on both sides of the chip. Such a device typically allow fluid flow rates of 1.5 μm/min.

In embodiments as illustrated in FIGS. 5-7, the microfluidic devices k (k=2, 3, 4) include two, three or more layers k1-k3, which layers embody two or more levels of the devices, as described earlier. That is, the multiple levels of the device are ensured by multiple layers. We note, however, that the number of levels involved in the device (typically three) may differ from the actual number of material layers used, which may greater or smaller, depending on the fabrication method actually used.

In detail, each of the devices shown in FIGS. 5-7 has nodes that have an identical structure. In FIGS. 6 and 7, the input channel k10, the output microchannels k1l, the cavity k23 and the inlet port k21 of the nodes are all formed in a first layer k1, whereas the distribution microchannels k3l are formed in a second layer k2. An additional, intermediate layer is needed in the designs of FIGS. 7A-7D. Yet, a microfluidic chip may be formed in a single injection molding step, as in FIG. 5. Thus, the present devices may effectively involve one, two, three (or even more) layers of materials, let alone possible cover/capping layers. In comparison, the device of FIG. 1 essentially involves one silicon layer, appropriately structured and then capped on each side.

Two mold components m1, m2 are relied on in FIG. 5, which are suitably structured, whereby a single injection molding step suffices to obtain a direct fabrication of the polymeric chip 2. That is, two mold inserts m1, m2 are used simultaneously for molding. One m1 of the mold inserts has two depth levels, i.e., one to fabricate the microchannels and the other one to fabricate the vias.

In FIG. 6, two layer components 31, 32 are composite, polymeric layers, obtained thanks to two mold inserts m1, m2a. The modl insert m1 of FIG. 6 is basically the same as the insert m1 of FIG. 5, whereas m2a is the mirror symmetric of m2. Two injection molding steps are involved in that case. I.e., the bottom layer 32 and top layer 31 are fabricated separately, by injecting material between each pair of mold components m1, m1a and m2a, m2b. The composite layers 31 and 32 are subsequently bonded. That is, on the one hand, the top layer and the vias and, on the other hand, the bottom layer, are fabricated independently using single mold inserts in two independent molding steps.

Figure 7A:
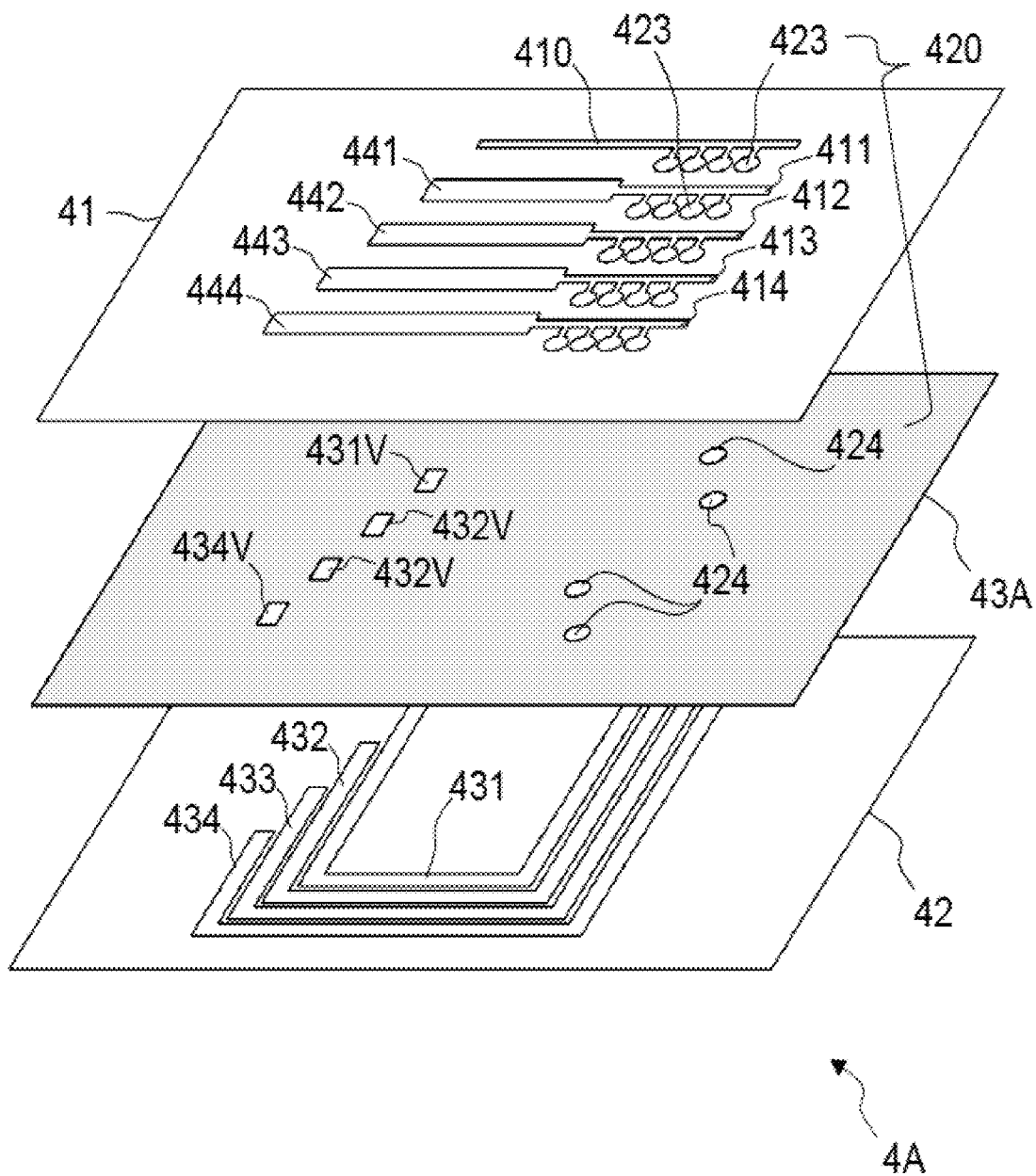
FIGS. 7A, 7B, 7C, and 7D show exploded views of three-layer devices (or part thereof), whose flow paths can advantageously be implemented on wicking media (e.g., paper), according to other embodiments.
Figure 7B:
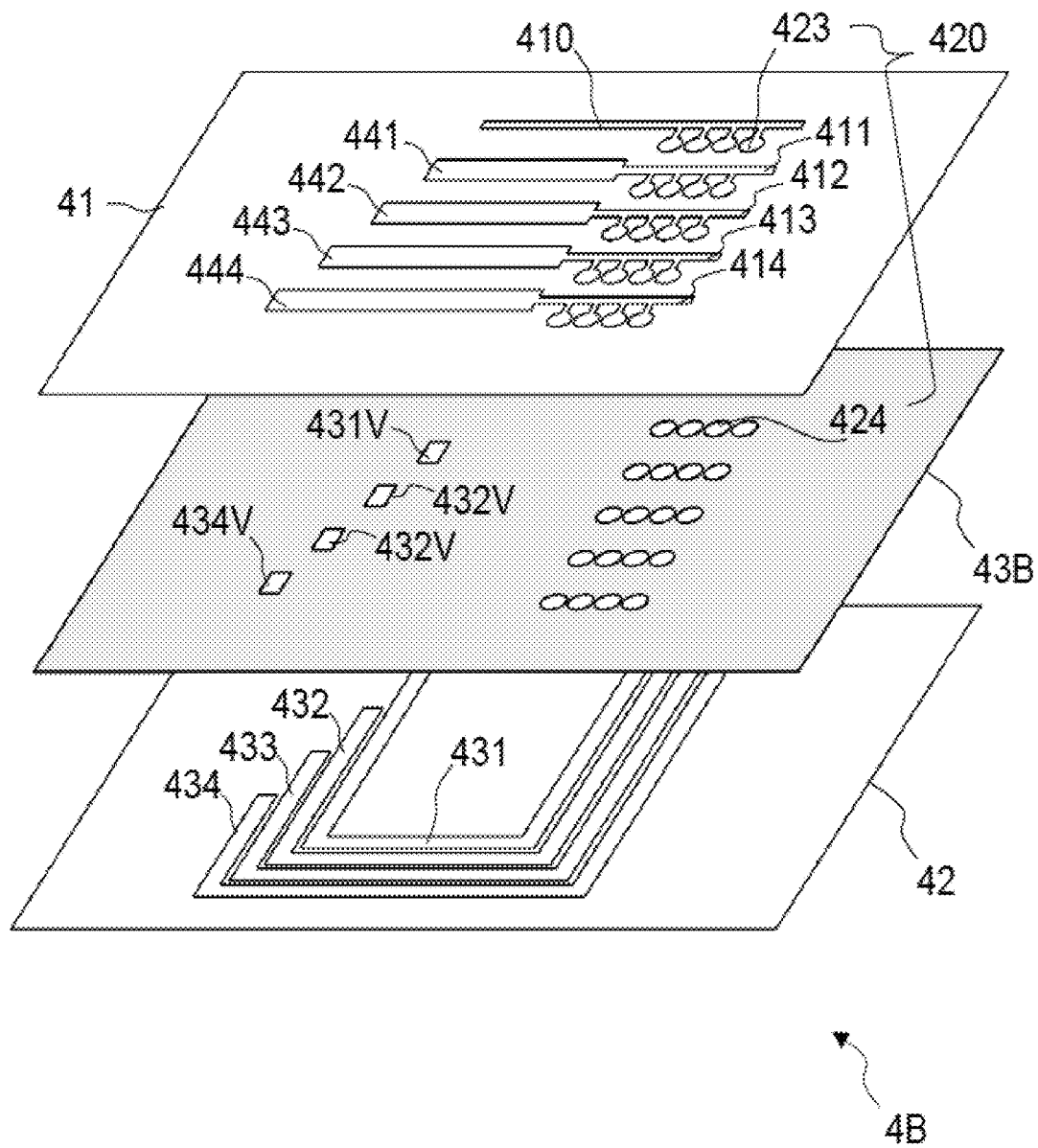
Figure 7C:
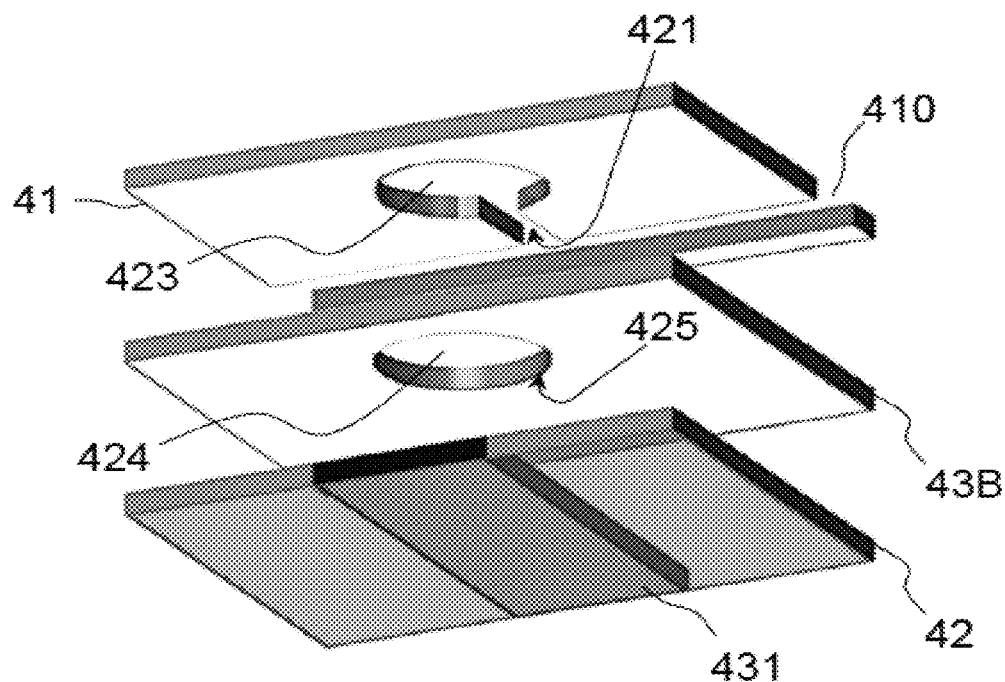
Figure 7D:
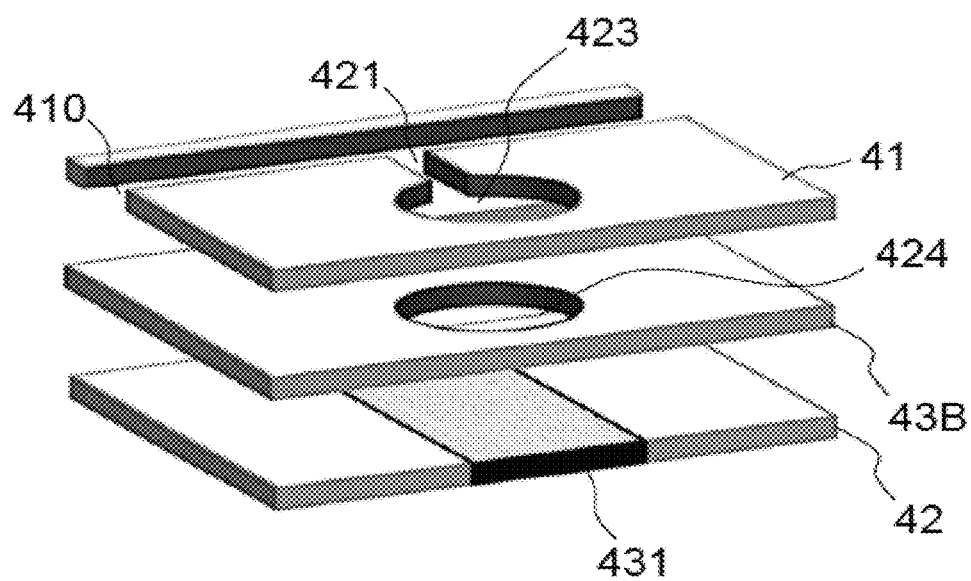
Figure 8:
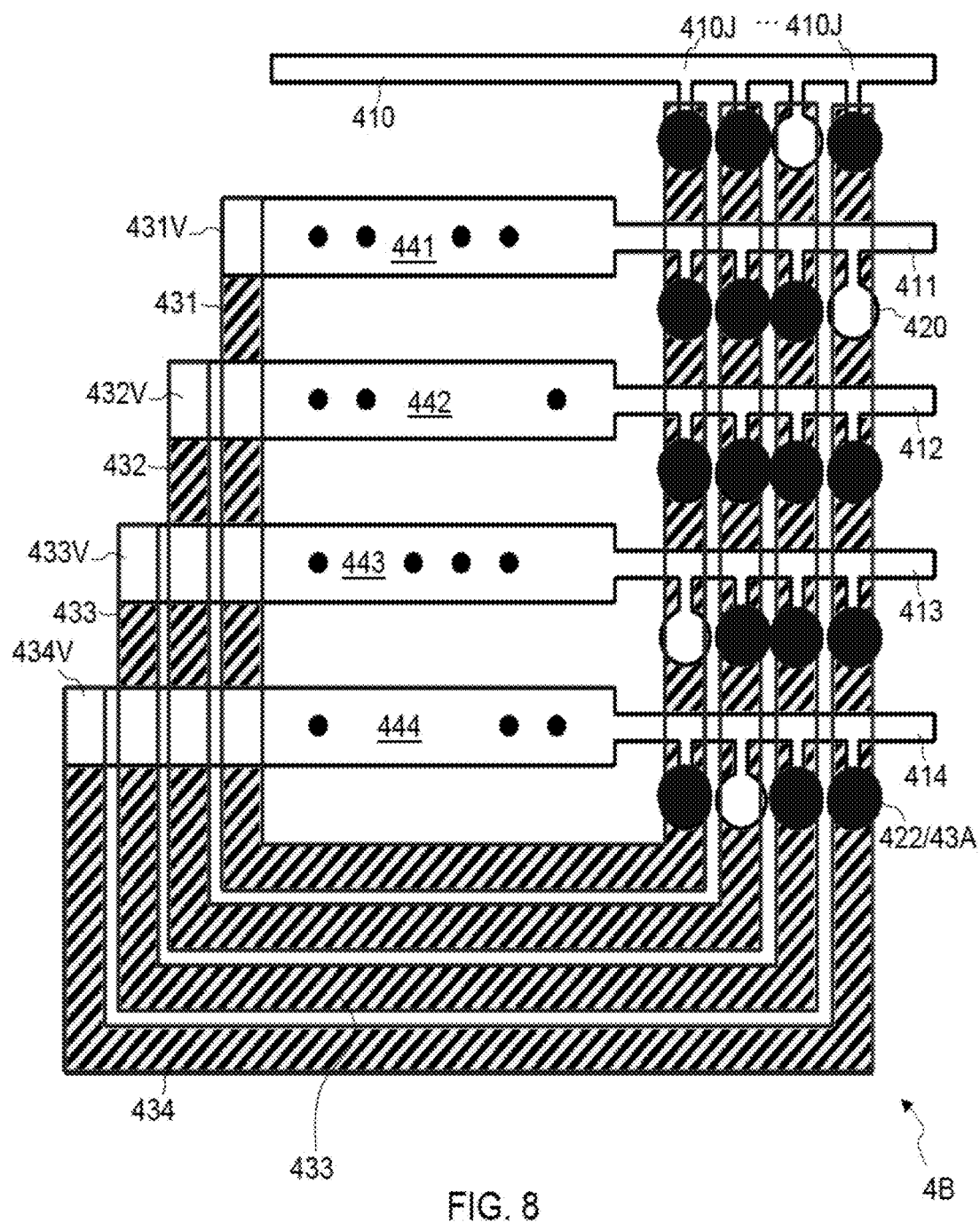
FIG. 8 schematically depicts a top view of a device according to FIG. 7A or FIG. 7B.

In embodiments such as illustrated in FIGS. 7-8, a wicking medium (like a fibrous/porous medium such as paper or a nitro-cellulosic material) is used as a basis to form the flow paths. The boundaries of the flow paths may for instance be formed by a hydrophobic material, such as wax (i.e., the flow paths are wax-printed). Namely, the input and output channels, the node cavities and inlet ports are defined on an upper layer 41, whereas distribution channels are defined on the lower layer 42.

Here, the vias 424 of the nodes 420 are formed in an intermediate layer 43A, 43B, placed between the first layer 41 and the second layer 42. The intermediate layer 43A, 43B may be provided as a thin polymeric film, separating the first and second layers 41, 42. Apertures may be opened in this film, at locations corresponding to the cavities 423, to define vias 424 and hence enable fluidic communication. Two different approaches can be contemplated, as respectively explored in FIGS. 7A and 7B, whereby the nodes 420 may be normally OFF (FIG. 7A, wherein the thin-film 43A mostly seals each cavity 423 from below) or normally ON (FIG. 7B, wherein the thin-film 43B is here punched to open each cavity 423).

Even though wicking media 41, 42 are used in the examples of FIGS. 7-8, as opposed to silicon in FIG. 1 or polymeric materials in FIGS. 5-6, a comparison of FIGS. 1, 5-6 and 7A-B shows that similar patterns of microchannels and cavities may nevertheless be achieved for the devices 1-4B. For example, in FIGS. 7-8, each cavity 423 is provided on a top level of the device (embodied by layer 41). Also, the cavities are formed as through holes in the top layer 41 (so as to be notably open on top). An inlet port 421 makes the junction between an inlet microchannel 410-414 and a respective cavity, on the first layer 41 (see also FIGS. 7C, 7D). Outlet microchannels 431-434 are provided in a lower level, embodied by layer 42 in FIG. 7. A suitable polymeric thin film 43A, 43B is inserted between the two layers 41, 42. Punched holes 424, 431V-434V play the role of vias. The lower edges of vias 424 play the role of outlet ports 425 of the cavities, which enable fluidic communication toward the lower microchannels 431-434.

The inserted film 43A, 43B may solely be punched at selected locations, in order to activate corresponding nodes (as in FIG. 7A). I.e., the device is normally OFF and selected nodes are activated in that case. In the embodiment of FIG. 7A, non-removed portions of the film 43A play the role of liquid blocking elements (see FIG. 8), which block liquid at the corresponding nodes.

Conversely, in the embodiment of FIG. 7B, the film 43B is punched at all node locations, so as for the device to be normally ON. This means that a subset of the nodes need be de-activated in that case. To that aim, a liquid blocking element 422 can be added in the cavities. This element 422 may for instance be formed by an alterable element, e.g., a hydrophobic barrier 422, placed in the cavity or otherwise sealing the latter. The hydrophobic barrier may for example be a removable substance (e.g., wax), inserted in the cavity.

Now, all cavities may systematically be filled with such hydrophobic barriers 422, thanks to an automated process, during a fabrication stage. This way, the device can be made normally OFF. Later on, an operator willing to customize the microfluidic template device may thus simply have remove selected ones of the hydrophobic barriers, such that only those nodes that effectively need be ON need be altered by the user. In general, one may seek to use liquid blocking elements 422 that are easily removable, such as wax, which can easily be melted or simply diluted in an appropriate chemical solvent, and then aspirated.

FIG. 8 shows a top view of a device according to 7B. FIG. 8 may also be regarded as resulting from the design of FIG. 7A, wherein the black disks corresponds to portions of the intermediate film 43A which have not been removed. Depending on the application targeted, the materials used, and the needed ratio of activated nodes to non-activated (or de-activated) nodes, one of the two approaches illustrated in FIGS. 7A and 7B may be more appropriate than the other.

Both the approaches of FIGS. 7A and 7B makes it possible to reconfigure the nodes as wax patches can be inserted and removed at will. Additional holes may easily be punched in the device of FIG. 7A and some of the holes may be sealed, e.g., using wax, if needed. Spotted chemicals 129 may also be removed and repositioned in a device as in FIG. 1 or 4. Yet, reconfiguring a chip as in FIG. 4 is more difficult, in principle, than reconfiguring a device as shown in FIGS. 7A and 7B.

In terms of dimensions, devices depicted in FIGS. 1, 4-6 are preferably dimensioned as follows. Each of the input microchannels, the distribution microchannels and the output microchannels have a depth that is between 10 and 100 µm (the depth is measured along axis z in FIG. 1). The depths of all channels (including inlet ports) may for instance be of about 20 µm. In addition, the input microchannel, the distribution microchannels and the inlet ports preferably have a same depth.

The width of the channels (as measured along axis x or y in FIG. 1) is typically between 10-200 µm (and preferably between 10 and 25 µm). The channel widths do, however, not play a critical role in the fluidic connections. The inlet port has a width that is preferably between 5 and 50 µm. In addition, the via has an average diameter that is typically between 25 and 200 µm (and preferably 50 and 100 µm), as measured in a plane parallel to (x, y). Relatively large dimensions of the vias are imposed so as not to add any additional hydraulic resistance at the level of the vias and not impair the fluidic connection. This, incidentally, also eases the fabrication of the vias. The thickness of the intermediate layer(s), in which the vias are formed, need typically be larger than 1 nm and is preferably larger than 1 µm, for mechanical robustness.

Such dimensions typically apply to chips, i.e., devices whose core chips are fabricated in silicon or injection molded. Devices relying on wicking media (FIGS. 7-8)

would typically differ, in dimensions. For example, wax-printed devices are preferably dimensioned as follows. The minimal (in-plane) width of wax-printed, lateral channel walls may be on the order of 300 µm (as after printing), and 850 µm (after heat treatment, due to the wax spreading). The depth is determined by the thickness of the wicking media (typically larger than 100 µm). The channel width (i.e., the in-plane separation between the wax-printed, lateral walls) may for example be between 100 µm and 1 000 µm, with a typical 50 µm standard deviation, after heat treatment. The modules' chambers may be wider, if necessary.

Embodiments have been described, in which simply fabricated arrays of nodes determines in which order a liquid passes through one or more microfluidic modules. In preferred embodiments, the array of nodes is programmed in a flexible manner by combining a fixed node geometry and by depositing chemicals in a subset of nodes. Such nodes are programmed to functionalize microfluidic chips, such that the effective liquid flow paths are configured after chip fabrication, e.g., by merely spotting chemicals. Thus, a universal microfluidic chip containing different microfluidic modules can be contemplated. Activating specific nodes determines the modules that will be used for specific needs.

In embodiments, microfluidic devices as discussed herein can be implemented as test devices, i.e., devices generally configured for diagnostic testing. I.e., at least one of the of m microfluidic modules has a flow path comprising reagents for enabling said diagnostic testing. Diagnostic testing relates to medical diagnostic and, more generally, to determining or analysis of the cause or nature of a problem or situation. Such test devices may notably be a portable, e.g., handheld device, such as for example a blood glucose meter, a dipstick or a test kit for detecting one or several analytes (e.g., homocysteine, C-reactive protein, glycated hemoglobin or HBA1C, HIV salivary assay, test for cardiac markers, tests for detecting allergens or genetically modified organisms, for the detection of pesticides and pollutants, etc.), or a pregnancy test. More generally, it may be any type of rapid diagnostic test (RDT) devices, i.e., devices used for quick and easy medical diagnostic tests. RDT devices typically allow results to be obtained within a few hours or less. They notably include point-of-care (POC) test devices and over-the-counter (OTC) tests. Furthermore, a test device as understood herein may be used to perform analyses going beyond medical diagnostic, for example for detecting toxins in water, etc. There are potentially numerous applications for such test devices, as the skilled person may realize.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, various material could be used for the microfluidic chips, such as polydimethylsiloxane (PDMS), glass or metal wafers. As another example, other types of valves, including passive or active microvalves may be contemplated, as known in the art.

The invention claimed is:

1. A microfluidic device comprising:
    an input microchannel;
    a set of m distribution microchannels, $m \geq 2$;
    a set of m microfluidic modules, in fluidic communication with the set of m distribution microchannels, respectively; and
    a set of m nodes, wherein one or more of the set of m nodes branches from the input microchannel and further branches to a respective one of the set of m distribution microchannels, to potentially ensure fluidic communication from the input microchannel to the respective one of the set of m distribution microchannels it branches to, wherein
        a subset, but not all, of the set of m nodes are altered, compared with remaining nodes of the set of m nodes, whereby the nodes in the set of m nodes have different liquid pinning strengths, such that the extent in which a liquid introduced in the input microchannel passes through one or more of the set of m microfluidic modules varies based on the different liquid pinning strengths, in operation.

2. The microfluidic device according to claim 1, wherein the subset of the set of m nodes are altered, compared with remaining nodes of the set of m nodes, wherein the one or more of the set of m nodes either pins a liquid thereat or lets a liquid pass there-through.

3. The microfluidic device according to claim 1, wherein the set of m nodes being a first set of m nodes, wherein one or more of the first set of m nodes branches from the input microchannel; and
the microfluidic device further comprises:
    a set of m output microchannels, wherein one or more of the set of m output microchannels connects to an output of a respective one or more of the set of m microfluidic modules; and
    m additional sets of m nodes each, whereby the microfluidic device comprises at least m+1 sets of m nodes, wherein
        the one or more of the set of m output microchannels branches into a respective one or more of the set of m nodes of a respective one or more of the m additional sets of m nodes;
        the respective one or more of the m additional sets of m nodes, wherein the respective one or more m nodes of the m additional sets of m nodes, branches to a respective one of the set of m distribution microchannels; and wherein
            a subset, but not all, of the m nodes of the respective one or more of the m additional sets of m nodes are altered, compared with remaining nodes of the set of m nodes, whereby the nodes in the set of m nodes have different liquid pinning strengths, such that the extent in which a liquid introduced in the input microchannel passes through one or more of the set of m microfluidic modules varies based on the different liquid pinning strengths of the first set of m nodes and the respective one or more of the m additional sets of m nodes, in operation.

4. The microfluidic device according to claim 3, wherein the one or more of the set of m nodes being configured to either pin a liquid thereat or let a liquid pass therethrough.

5. The microfluidic device according to claim 4, wherein the respective one or more of the m additional sets of m nodes and the respective one of the set of m distribution microchannels are configured to effectively prevent liquid, exhausted by one or more of the set of m microfluidic modules, to later re-enter the same one or more of the set of m microfluidic modules.

6. The microfluidic device according to claim 3, wherein the m+1 sets of m nodes are arranged as an array of m×(m+1) nodes, in a crossbar switch configuration.

7. The microfluidic device according to claim 6, wherein the microfluidic device comprises distinct, parallel levels, including a first level and a second level; and
both the input microchannel and the set of m output microchannels are defined on the first level, whereas the set of m distribution microchannels are defined on the second level.

8. The microfluidic device according to claim 7, wherein at least a subset of the nodes of the m+1 sets of m nodes comprise, each:
a cavity, formed on the first level, the cavity being open on a top side;
an inlet port, on the first level, the inlet port branching from the input microchannel or one of the set of m output microchannels and communicating with the cavity through an ingress of the cavity;
an outlet port, branching to one of the set of m distribution microchannels on the second level; and
a via extending from the cavity to the outlet port, for the cavity to communicate with the outlet port, wherein the cavity comprises a liquid blocking element configured to prevent an aqueous liquid filling the inlet port to reach the outlet port.

9. The microfluidic device according to claim 8, wherein the via extends on a third level of the microfluidic device, between the first level and the second level, from a bottom side of the cavity down to the outlet port, wherein the bottom side of the cavity is opposite to a top side of the cavity.

10. The microfluidic device according to claim 8, wherein the liquid blocking element being a liquid pinning structure formed at the ingress of the cavity, the pinning structure configured to prevent the aqueous liquid filling front at the ingress of the cavity.

11. The microfluidic device according to claim 10, wherein
the liquid pinning structure being formed by an opening angle $\theta_1$ of the cavity, the opening angle is between 60° and 160°.

12. The microfluidic device according to claim 11, wherein
the ingress of the cavity has a width that is smaller than a depth of the cavity; and
walls of the cavity, on each side of the ingress, are separated by a gap corresponding to the width, wherein the walls form two opposite opening angles $\theta_1$ in the cavity, the opening angles, respectively, are between 60° and 160°.

13. The microfluidic device according to claim 10, wherein
the cavity comprises a wetting material arranged at the liquid pinning structure, to allow the aqueous liquid filling the inlet port to reach the outlet port, notwithstanding the liquid pinning structure.

14. The microfluidic device according to claim 8, wherein the liquid blocking element is an alterable element, placed in the cavity or sealing the bottom side of the cavity, which is opposite the top side of the cavity.

15. The microfluidic device according to claim 8, wherein inlet ports of two nodes of a same set of nodes have different hydraulic resistances.

16. The microfluidic device according to claim 15, wherein
the input microchannel, the one or more of the set of m distribution microchannels, and the one or more of the set of m output microchannels have a depth that is between 10 and 100 µm;
the input microchannel, the one or more of the set of m distribution microchannels, and the inlet port have a same depth;
the inlet port has a width between 5 and 50 µm; and
the via has an average diameter between 25 and 200 µm, as measured parallel to a mid-plane of the first level from the second level.

17. The microfluidic device according to claim 8, wherein the outlet port comprises a fluid flow constriction valve, so as to prevent an aqueous liquid in the set of m distribution microchannels, branched by the outlet port, to reach the via.

18. The microfluidic device according to claim 8, wherein the outlet port branches to the respective one of the set of m distribution microchannels, at a level of a junction, the respective one of the set of m distribution microchannels comprising a fluid flow constriction valve on one side at the level of the junction, so as to force an aqueous liquid exhausted through the outlet port toward a direction that extends from the one side at the level of the junction to an opposite side at the level of the junction.

19. The microfluidic device according to claim 18, wherein
the fluid flow constriction valve on one side at the level of the junction is formed by a first section and a second section of the respective one of the set of m distribution microchannels, the first section being tapered and leading to the second section, the second section having a larger average diameter than the first section, so as to provide an opening angle $\theta_2$ in the second section which is between 60° and 160°.

20. The microfluidic device according to claim 8, wherein the microfluidic device comprises at least two layers; and
the input microchannel, the one or more of the set of m output microchannels, the cavity and the inlet port are all formed in a first layer of the at least two layers, whereas the one or more of the set of m distribution microchannels are formed in a second layer of the at least two layers.

21. The microfluidic device according to claim 20, wherein
the via being formed in an intermediate layer of the microfluidic device, between the first layer of the at least two layers and the second layer of the at least two layers.

22. The microfluidic device according to claim 1, wherein the set of m microfluidic modules comprise:
an optical detection chamber to enable optical detection; and
one or both of: a fluid mixing chamber and a reaction chamber.

23. The microfluidic device according to claim 1, wherein m≥3 and the set of m microfluidic modules each comprise:
- an optical detection module, configured in the microfluidic device to enable optical detection of analyte therein;
- one or more fluid mixing modules; and
- a reaction module.

24. A microfluidic device comprising:
- an input microchannel;
- at least two microfluidic modules;
- a first set of at least two nodes, connecting the input microchannel to at least two microfluidic modules; and
- a second set of at least two nodes, connecting a respective ordered pair of two of the at least two microfluidic modules, wherein
  - subsets of nodes of each of the first set of at least two nodes and the second set of at least two nodes are altered, compared with remaining nodes of the first set and the second set, the subsets of nodes having different liquid pinning strengths in the first set of at least two nodes and the second set of at least two nodes, wherein the extent that a liquid introduced in the input microchannel passes through the respective ordered pair of two of the at least two microfluidic modules varies based on the different liquid pinning strengths, in operation.

25. A method of programming a microfluidic device, comprising:
- providing a microfluidic device, wherein the microfluidic device comprises:
  - an input microchannel;
  - a set of m distribution microchannels, m≥2;
  - a set of m microfluidic modules, in fluidic communication with the set of m distribution microchannels, respectively; and
  - a set of m nodes, branching from the input microchannel and further branching to one distribution microchannel of the set of m distribution microchannels, to potentially ensure fluidic communication from the input microchannel to the set of m distribution microchannels it branches to; and
- altering a subset, but not all, of the set of m nodes, so the set of m nodes have different liquid pinning strengths, such that the extent in which a liquid introduced in the input microchannel reaches one or more of the set of m microfluidic modules varies based on the different liquid pinning strengths, in operation.

* * * * *